US012569181B2

(12) United States Patent
Yang et al.

(10) Patent No.: US 12,569,181 B2
(45) Date of Patent: Mar. 10, 2026

(54) ECG WAVEFORM DISPLAY METHOD AND MEDIUM THEREOF, AND ELECTRONIC DEVICE

(71) Applicant: Huawei Technologies Co., Ltd., Shenzhen (CN)

(72) Inventors: Bin Yang, Shenzhen (CN); Shuo Wang, Shenzhen (CN); Wenjuan Chen, Shenzhen (CN); Hao Xiong, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 323 days.

(21) Appl. No.: 18/042,916

(22) PCT Filed: Aug. 24, 2021

(86) PCT No.: PCT/CN2021/114341
§ 371 (c)(1),
(2) Date: Feb. 24, 2023

(87) PCT Pub. No.: WO2022/042558
PCT Pub. Date: Mar. 3, 2022

(65) Prior Publication Data
US 2023/0309896 A1 Oct. 5, 2023

(30) Foreign Application Priority Data
Aug. 25, 2020 (CN) .......................... 202010862902.1

(51) Int. Cl.
*A61B 5/339* (2021.01)
*A61B 5/00* (2006.01)
(Continued)

(52) U.S. Cl.
CPC .............. *A61B 5/339* (2021.01); *A61B 5/332* (2021.01); *A61B 5/349* (2021.01); *A61B 5/681* (2013.01);
(Continued)

(58) Field of Classification Search
CPC ............................... A61B 5/339; A61B 5/349
(Continued)

(56) References Cited

U.S. PATENT DOCUMENTS 10,998,101 B1 * 5/2021 Tran ....................... G16H 50/30
2019/0223773 A1 7/2019 Galm et al.

FOREIGN PATENT DOCUMENTS

| CN | 103941874 A | 7/2014 |
| CN | 110299100 A | 10/2019 |
| CN | 113080982 A | 7/2021 |

* cited by examiner

*Primary Examiner* — Nadia A Mahmood
(74) *Attorney, Agent, or Firm* — Slater Matsil, LLP

(57) ABSTRACT

An ECG waveform display method is provided. The method includes: An electronic device starts an ECG waveform detection application, to collect an ECG waveform; the electronic device reads wearing part data between the electronic device and a wrist of a user, where the wearing part data is obtained through IMU wearing part identification; the electronic device determines first wearing part information based on wearing status data, and the determined state is a first determined state or a second determined state; the electronic device obtains second wearing part information between the electronic device and the wrist of the user through ECG wearing part identification; and when the first wearing part information and the second wearing part information are the same and indicate a determined state, the electronic device displays the ECG waveform on a display in a display manner corresponding to the determined state.

20 Claims, 12 Drawing Sheets

(51) Int. Cl.
  *A61B 5/332*   (2021.01)
  *A61B 5/349*   (2021.01)
(52) U.S. Cl.
  CPC .... *A61B 5/6844* (2013.01); *A61B 2562/0219*
              (2013.01)
(58) Field of Classification Search
  USPC ........................................................ 600/523
  See application file for complete search history.

100

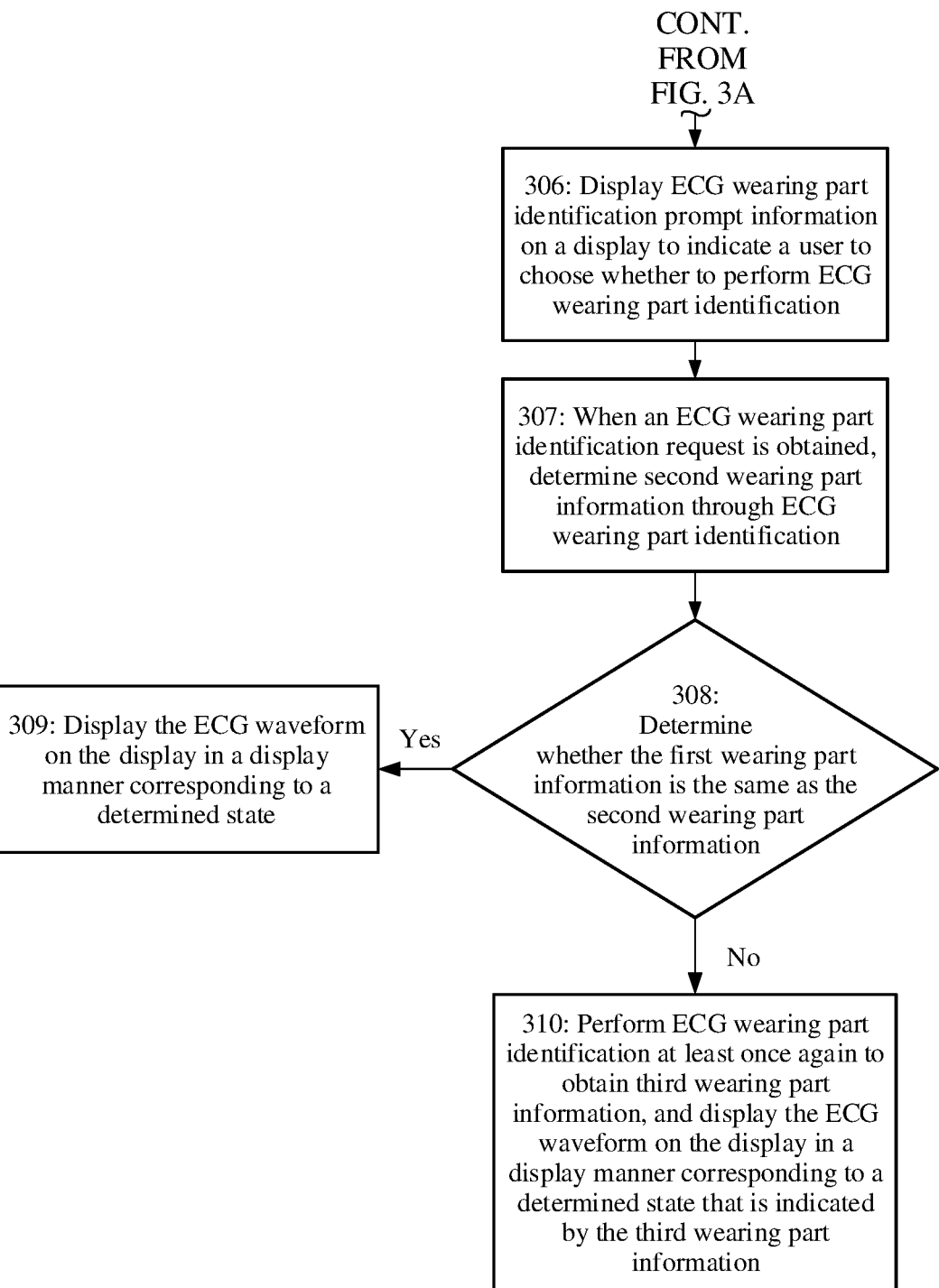

CONT.
FROM
FIG. 3A

306: Display ECG wearing part identification prompt information on a display to indicate a user to choose whether to perform ECG wearing part identification 307: When an ECG wearing part identification request is obtained, determine second wearing part information through ECG wearing part identification 308: Determine whether the first wearing part information is the same as the second wearing part information 309: Display the ECG waveform on the display in a display manner corresponding to a determined state Yes No 310: Perform ECG wearing part identification at least once again to obtain third wearing part information, and display the ECG waveform on the display in a display manner corresponding to a determined state that is indicated by the third wearing part information

FIG. 3B

ECG WAVEFORM DISPLAY METHOD AND MEDIUM THEREOF, AND ELECTRONIC DEVICE

CROSS-REFERENCE TO RELATED APPLICATIONS

This application is a National Stage of International Patent Application No. PCT/CN2021/114341, filed on Aug. 24, 2021, which claims priority to Chinese Patent Application No. 202010862902.1, filed on Aug. 25, 2020, both of which are hereby incorporated by reference in their entireties.

TECHNICAL FIELD

This application relates to the field of electronic technologies, and in particular, to an ECG waveform display method and medium thereof, and an electronic device.

BACKGROUND

An electrocardiogram (electrocardiogram, ECG) can reflect a health status of a user. For example, the ECG can reflect a heart disease (for example, a heart rate abnormality) or the like. With continuous development of wearable devices such as a smart wrist strap and a smart watch, currently, a health detection function like ECG detection may be integrated into a wearable device such as a smart watch, to monitor a physical sign such as a heart rate of a user, so that prediction for a physical status of the user is implemented and a cardiac conduction electronic device disorder or myocardial lesion is effectively avoided.

When the user performs ECG detection by using the wearable device, an ECG waveform is directly related to a position of a left hand or a right hand on which the user wears the wearable device. For example, if the user wears the wearable device on the left hand, and then touches an electrode of the wearable device with the right hand of the user, an ECG waveform generated by the wearable device is a forward waveform. Without changing any configuration of the wearable device, if the user wears the wearable device on the right hand, and then touches an electrode of the wearable device with the left hand of the user, an ECG waveform generated by the wearable device is an incorrect reverse waveform.

To determine whether the user wears the wearable device on the left hand or the right hand, a deflection angle of the smart wearable device when the user wears the wearable device may be detected and obtained based on a built-in inertial measurement unit in the wearable device, to identify whether the user wears the wearable device on the left hand or the right hand. However, when the user wears the wearable device for the first time and keeps in a static state, if the ECG detection function is instantly used, whether the wearable device is worn on the left hand or the right hand cannot be determined, and therefore whether the ECG waveform is normally displayed cannot be determined.

In another solution for determining whether the user wears the wearable device on the left hand or the right hand, when the user enables the ECG detection function of the wearable device, an ECG waveform generated by the wearable device is compared with a preset reference waveform, so that whether the user wears the wearable device on the left hand or the right hand is identified. However, in a case in which a heart of a user is rightward, when the user wears a wearable device on a left hand, a feature of an ECG waveform generated by the wearable device is similar to a feature of an ECG waveform generated when a user whose heart location is normal wears a wearable device on a right hand. Consequently, a misjudgment easily occurs.

SUMMARY

Embodiments of this application provide an ECG detection method and apparatus based on left/right hand identification, a medium, and an electronic device.

According to a first aspect, an embodiment of this application provides an ECG waveform display method. The method includes:

an electronic device starts an ECG waveform detection application, to collect an ECG waveform;

the electronic device reads wearing part data between the electronic device and a wrist of a user, where the wearing part data is obtained through IMU wearing part identification;

the electronic device determines first wearing part information based on the wearing status data, where the first wearing part information includes a determined state and an uncertain state, and the determined state is a first determined state or a second determined state;

the electronic device obtains second wearing part information between the electronic device and the wrist of the user through ECG wearing part identification; and the electronic device displays, when the first wearing part information and the second wearing part information are the same and indicate a determined state, the ECG waveform on a display in a display manner corresponding to the determined state.

In this embodiment of this application, a false positive rate of determining whether the ECG waveform is displayed in a normal display manner can be reduced, and accuracy of displaying the ECG waveform in a normal display manner can be improved.

In a possible implementation of the first aspect, that the ECG waveform is displayed, when the first wearing part information and the second wearing part information are the same and indicate a determined state, on a display in a display manner corresponding to the determined state includes:

the electronic device displays the ECG waveform on the display in a normal display manner when the first wearing part information and the second wearing part information are the same as preset wearing part information.

In a possible implementation of the first aspect, that the ECG waveform is displayed, when the first wearing part information and the second wearing part information are the same and indicate a determined state, on a display in a display manner corresponding to the determined state includes:

when the first wearing part information and the second wearing part information are different from preset wearing part information, the electronic device adjusts the ECG waveform, so that the ECG waveform is displayed on the display in a normal display manner.

In a possible implementation of the first aspect, the method further includes: when the first wearing part information and the second wearing part information indicate a determined state but are different, ECG wearing part identification is performed at least once again to obtain third wearing part information; and the electronic device displays the ECG waveform on the display in a display manner corresponding to a determined state that is indicated by the third wearing part information.

In this embodiment of this application, both IMU wearing part identification and ECG wearing part identification are used, and when pieces of wearing information determined by the IMU wearing part identification and the ECG wearing part identification are different, a quantity of ECG wearing part identification times and an ECG detection confidence level proportion are increased. Therefore, to some extent, accuracy of displaying a wearing part and the ECG waveform in a normal state is improved.

In a possible implementation of the first aspect, the method further includes: when the first wearing part information indicates an uncertain state, ECG wearing part identification is performed to obtain fourth wearing part information; and the electronic device displays the ECG waveform on the display in a display manner corresponding to a determined state that is indicated by the fourth wearing part information.

In a possible implementation of the first aspect, the method further includes: when the first wearing part information and the fourth wearing part information are the same and indicate an uncertain state, ECG wearing part identification is performed at least once again to obtain fifth wearing part information; and the electronic device displays the ECG waveform on the display in a display manner corresponding to a determined state that is indicated by the fifth wearing part information.

In this embodiment of this application, both IMU wearing part identification and ECG wearing part identification are used, and when pieces of wearing information determined by the IMU wearing part identification and the ECG wearing part identification are different, a quantity of ECG wearing part identification times and an ECG detection confidence level proportion are increased. Therefore, to some extent, accuracy of displaying a wearing part and the ECG waveform in a normal state is improved.

In a possible implementation of the first aspect, that the electronic device determines first wearing part information based on the wearing status data includes:

obtaining a first wearing part confidence level based on the wearing status data, and determining the first wearing part information based on at least the first wearing part confidence level.

In a possible implementation of the first aspect, the obtaining a first wearing part confidence level based on the wearing status data, and determining the first wearing part information based on at least the first wearing part confidence level includes:

obtaining a plurality of first wearing part confidence levels based on the wearing status data;
processing the plurality of first wearing part confidence levels according to a first iteration formula, to obtain a first average wearing part confidence level; and
determining the first wearing part information based on the first average wearing part confidence level.

In a possible implementation of the first aspect, the wearing part data includes an acceleration value and an attitude angle that are detected by an IMU, and the obtaining a first wearing part confidence level based on the wearing status data includes:

obtaining the first wearing part confidence level based on the acceleration value and the attitude angle that are detected by the IMU.

In a possible implementation of the first aspect, the obtaining the first wearing part confidence level based on the acceleration value and the attitude angle that are detected by the IMU includes:

inputting a currently obtained standard deviation and average value of accelerations of an accelerometer on an X-axis, a Y-axis, and a Z-axis, and a standard deviation and average value of attitude angles of a gyroscope on the X-axis, the Y-axis, and the Z-axis into a trained IMU wearing part identification model, where an output result of the trained IMU wearing part identification model is the first wearing part confidence level.

In a possible implementation of the first aspect, that the second wearing part information is obtained through ECG wearing part identification includes:

obtaining a second wearing part confidence level through ECG wearing part identification, and determining the second wearing part information based on at least the second wearing part confidence level.

In a possible implementation of the first aspect, the obtaining a second wearing part confidence level through ECG wearing part identification, and determining the second wearing part information based on at least the second wearing part confidence level includes:

obtaining a plurality of first wearing part confidence levels based on the wearing status data;
processing the plurality of first wearing part confidence levels according to a first iteration formula, to obtain a first average wearing part confidence level;
determining the first wearing part information based on the first average wearing part confidence level;
obtaining a plurality of second wearing part confidence levels through ECG wearing part identification;
obtaining a second average wearing part confidence level based on the first average wearing part confidence level, the plurality of second wearing part confidence levels, and a second iteration formula; and
obtaining the second wearing part information based on the second average wearing part confidence level.

In a possible implementation of the first aspect, the obtaining a second wearing part confidence level through ECG wearing part identification includes:

determining the second wearing part confidence level based on waveform feature information of the ECG waveform.

In a possible implementation of the first aspect, the waveform feature information of the ECG waveform is input into a trained ECG wearing part identification model, to obtain an output result of the trained ECG wearing part identification model that is the second wearing part confidence level.

In a possible implementation of the first aspect, the first iteration formula is CI1_average=a1*CI1_average+b1*CI_imui, where CI1_average represents the first average wearing part confidence level, CI_imui represents the first wearing part confidence level, a1 and b1 are natural numbers, a sum of a1 and b1 is 1, and a is greater than b.

In a possible implementation of the first aspect, the second iteration formula is CI2_average=a2*CI1_average+b2*CI_ecgi, where CI2_average represents the second average wearing part confidence level, CI_ecgi represents the second wearing part confidence level, a2 and b2 are natural numbers, a sum of a2 and b2 is 1, and a2 is less than b2.

In a possible implementation of the first aspect, the waveform feature information of the ECG waveform includes:

QRS wave area, a ratio of a QR width to an RS width, a QR height, an RS height, a P wave amplitude, P wave area (including positive and negative values), a T wave width, and T wave area.

In a possible implementation of the first aspect, that ECG wearing part identification is performed at least once again to obtain third wearing part information includes:

performing iteration processing on the second wearing part confidence level and the third wearing part confidence level, to obtain a third average wearing part confidence level, where the second wearing part confidence level is obtained through the previous ECG wearing part identification, and the second wearing part confidence level corresponds to the second wearing part information; and determining the third wearing part information based on the third average wearing part confidence level.

In a possible implementation of the first aspect, the determined state is that a wearing state between the electronic device and the wrist of the user is a right-hand wearing state or a left-hand wearing state.

According to a second aspect, an embodiment of this application provides a readable medium. The readable medium stores instructions. When the instructions are executed on an electronic device, a machine is enabled to perform the ECG waveform display method according to the first aspect.

According to a third aspect, an embodiment of this application provides an electronic device, including:

a memory, configured to store instructions executed by one or more processors of the electronic device; and a processor that is one of the processors of the electronic device, configured to perform the ECG waveform display method according to the first aspect.

BRIEF DESCRIPTION OF THE DRAWINGS

FIG. 3A to FIG. 3C are a schematic flowchart of an ECG waveform display method according to some embodiments of this application;

DETAILED DESCRIPTION OF ILLUSTRATIVE EMBODIMENTS

Illustrative embodiments of this application include, but are not limited to, an ECG waveform display method and medium thereof, and an electronic device.

The following further describes embodiments of this application in detail with reference to accompanying drawings.

Figure 1A:
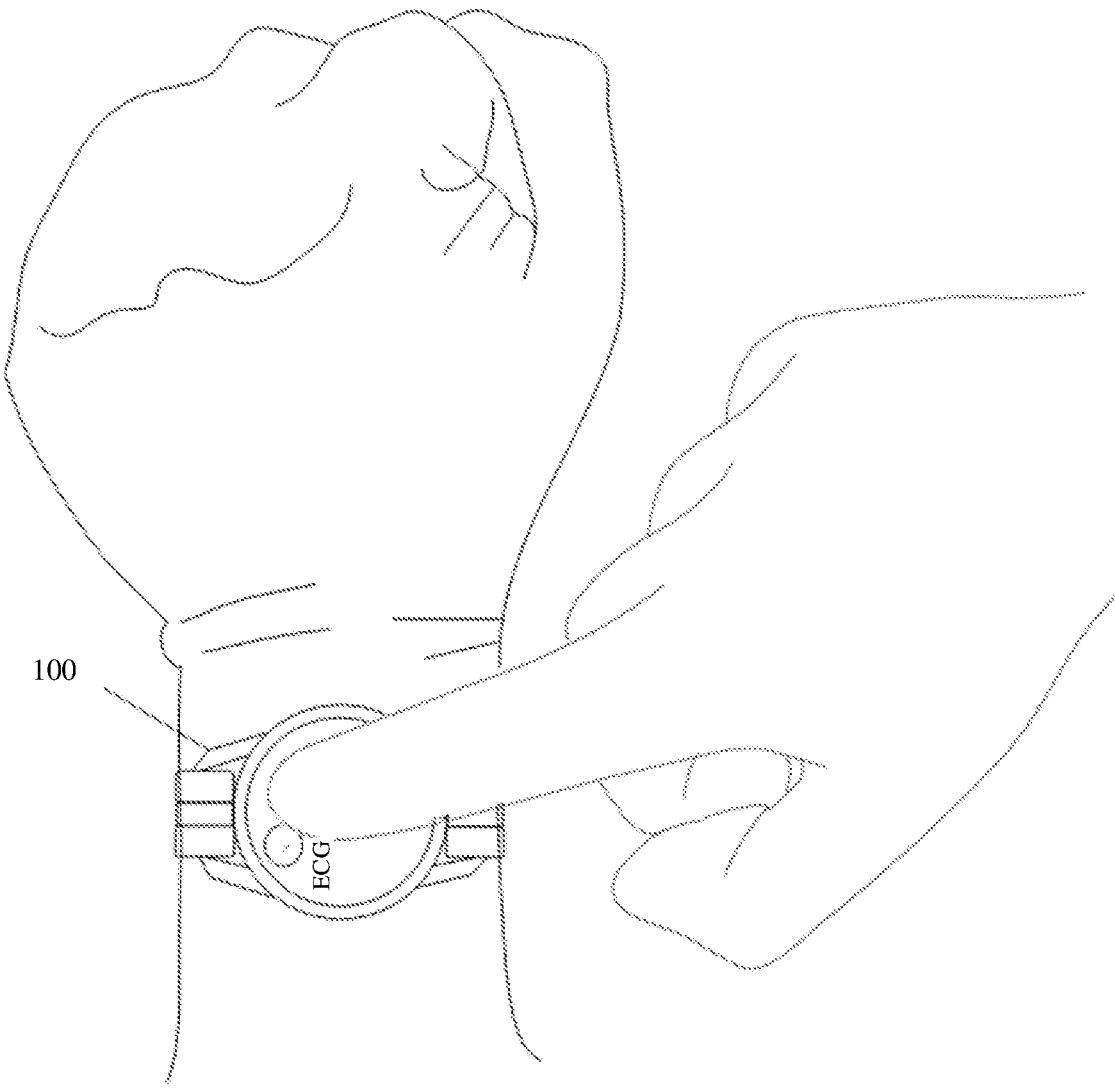
FIG. 1A is a diagram of an application scenario of an ECG waveform display method according to some embodiments of this application.
Figure 1B:
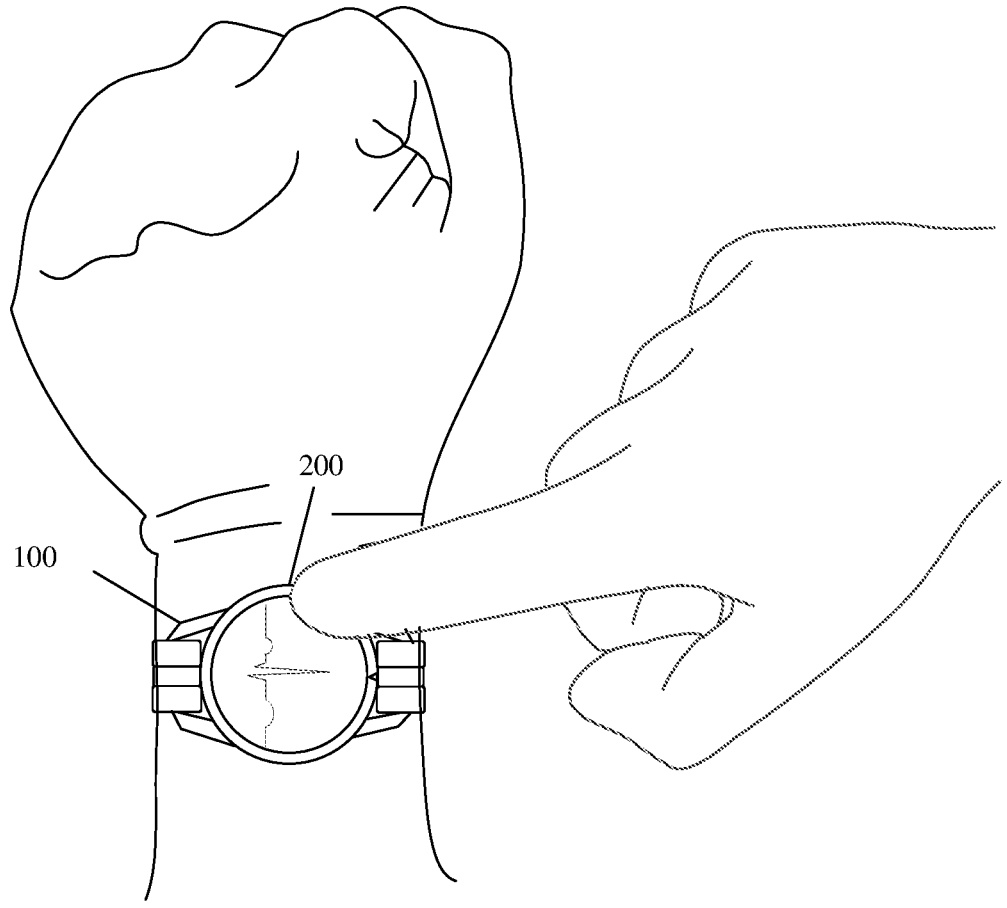
FIG. 1B is a diagram of an application scenario of an ECG waveform display method according to some embodiments of this application.
Figure 1C:
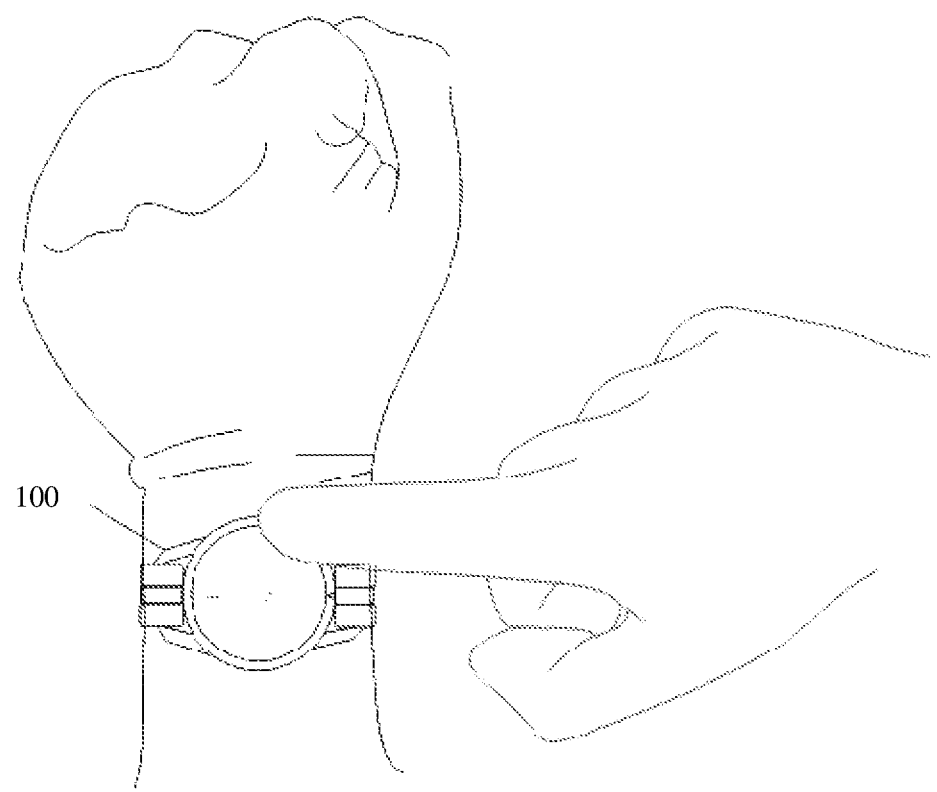
FIG. 1C is a diagram of an application scenario of an ECG waveform display method according to some embodiments of this application.

FIG. 1A, FIG. 1B, and FIG. 1C are a diagram of an application scenario of an ECG waveform display method according to some embodiments of this application. In the embodiment shown in FIG. 1A, FIG. 1B, and FIG. 1C, a wearable device 100 may perform the ECG waveform display method provided in this application. The wearable device 100 is equipped with a built-in ECG detection module, a plurality of built-in electrodes, and a built-in inertial measurement unit (Inertial measurement unit, IMU). For example, the wearable device 100 includes two electrodes, and the two electrodes are respectively denoted as an electrode A and an electrode B. As shown in FIG. 1B, the electrode A 200 is disposed on a side surface of a housing of the wearable device 100, and the electrode B (not shown in the figure) is disposed on a lower surface of the wearable device 100. In some embodiments, a user wears the wearable device 100 with the built-in ECG detection module to perform electrocardiogram function detection. For example, the user wears the wearable device 100 on a left wrist of the user. In this case, the left wrist of the user is in contact with the electrode B on the lower surface of the wearable device 100. The user acts on an icon of an ECG waveform detection APP (Application, application) that is used to perform electrocardiogram detection. For example, when the user taps the ECG waveform detection APP by using a finger, as shown in FIG. 1A, or when the user sends, to the wearable device 100 in a voice manner, a command for starting the ECG APP, the wearable device 100 detects a tap operation for starting the ECG APP or receives a command for starting the ECG APP, and enables an ECG detection function. The user may use a right finger of the user to contact the electrode A 200 on the side surface of the wearable device 100. As shown in FIG. 1B, the electrode A 200 and the electrode B form an electrode pair, and detailed information about a decrease of a ventricular depolarization waveform of the user passing through a heart tissue can be collected. The ECG detection module performs processing such as analog-to-digital conversion and filtering on the electrical signals collected by the electrode A 200 and the electrode B, to generate a single-lead ECG signal of the user. The wearable device 100 displays, on a display, an ECG waveform that is of the user and that is generated by the ECG detection module. As shown in FIG. 1B, a smart watch 100 is set to display an ECG waveform in a normal display manner when the smart watch 100 is worn on a right hand. For example, a peak of the ECG waveform faces a left-hand side. However, when the smart watch 100 is worn by the user on the left wrist, the peak of the ECG waveform faces a right-hand side, and looks abnormal. The ECG waveform is displayed on the display in an abnormal display manner. In this embodiment of this application, the wearable device 100 determines, based on the built-in IMU, whether the user wears the wearable device on the left hand or the right hand, and further determines, based on the ECG waveform generated by the ECG detection module, whether the user wears the wearable device on the left hand or the right hand. Further, as shown in FIG. 1C, the wearable device 100 displays the ECG waveform on the display in a normal display manner based on the determining result, to facilitate viewing by the user.

In this way, compared with a solution in a related technology in which left-hand and right-hand determining is performed only based on an IMU, or left-hand and right-hand determining is performed only based on a collected ECG waveform, in this embodiment, a problem that a determining error rate is high because left-hand and right-hand determining is performed only based on an IMU can be avoided. In addition, a problem of excessively long time consumption caused by performing left-hand and right-hand determining only based on an ECG waveform can be avoided. In this way, a determining time period is shortened, and accuracy of left-hand and right-hand identification and accuracy of displaying an ECG waveform in a normal state are improved.

In some embodiments, the wearable device 100 may further analyze an electrocardiogram of the user based on an ECG waveform generated by the ECG detection module, and display an analysis result on the display of the wearable device 100 in a text form, or play an analysis result in a voice form, so that the user can learn about a health status of the user's heart more intuitively.

In the embodiment shown in FIG. 1, the wearable device 100 may independently collect ECG data, determine a left hand or right hand, and display a final ECG waveform or generate an electrocardiogram report based on a result of determining the left hand or right hand.

It may be understood that although FIG. 1A, FIG. 1B, and FIG. 1C show the smart watch 100, an electronic device applicable to the ECG waveform display method in this application may be another wrist wearing device, for example, a smart band or another dedicated device that is worn on a wrist and that has an electrocardiogram measurement function.

A processing process described in this application, for example, a process of performing calculation and determining based on data, may be performed on a smart band, a smartphone, or another device that can be worn on a wrist. Alternatively, the process may be performed on a device such as a mobile phone, a tablet computer, a personal digital assistant (personal digital assistant, PDA), or a notebook computer that is wirelessly or wiredly connected to a smart band, a smartphone, or another device that can be worn on a wrist.

The following describes in detail, by using an example in which the wearable device 100 is the smart watch 100, a technical solution in which a user wears the wearable device that can perform the ECG waveform display method provided in this application.

Figure 2:
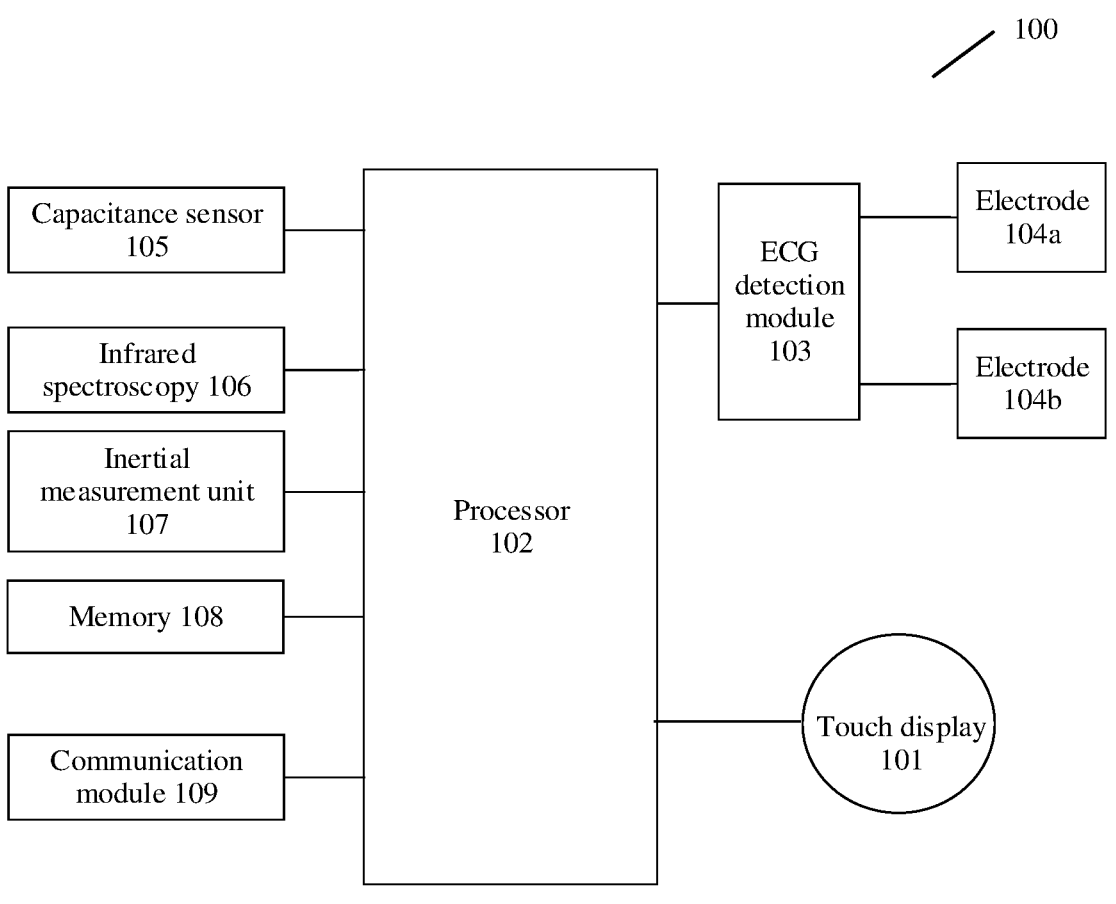
FIG. 2 is a block diagram of a structure of a smart watch according to some embodiments of this application.

FIG. 2 is a block diagram of a structure of a smart watch 100 according to some embodiments of this application. As shown in FIG. 2, the smart watch 100 includes a touch display 101, a processor 102, an ECG detection module 103, an electrode 104a, an electrode 104b, a capacitance sensor 105, an IMU 104, an infrared spectroscopy (Infrared Spectroscopy, IR) 106, an inertial measurement unit (Inertial measurement unit, IMU) 107, a memory 108, a communication module 109, and the like.

In one aspect, the touch display 101 may be used as a touch panel to collect a touch operation of a user on the touch display 101, and drive a responding connection apparatus according to a preset program. For example, a touch operation of tapping an ECG APP icon of the smart watch 100 by the user by using a finger is collected. In another aspect, the touch display 101 may be configured to display information input by the user or prompt information provided for the user, and various menus on the smart watch 100. For example, an ECG waveform of the user, an electrocardiogram report of the user, and the like that are detected by using the smart watch 100 are displayed.

The processor 102 includes a plurality of processing units, and may run software code of the ECG waveform display method provided in some embodiments of this application. For example, wearing part information is determined through IMU wearing part identification and ECG wearing part identification, to determine whether the ECG waveform is displayed in a normal display manner. If the ECG waveform is not displayed in a normal display manner, the ECG waveform is adjusted to an ECG waveform displayed in a normal display manner, an electrocardiogram report of the user, and the like.

The ECG detection module 103 is configured to process, into an ECG waveform, electrical signals of a human body detected by the electrode 104a and the electrode 104b. For example, the ECG detection module 103 may internally include one or more filters, or the ECG detection module 103 may be connected to one or more filters. The one or more filters may be configured to perform filtering processing on human body electrical signals detected by the electrode 104a and the electrode 104b. For example, the ECG detection module 103 may be configured with frequency domain bandwidths of the one or more filters. When the frequency bandwidth of the filter is 0.5 Hz to 40 Hz, the filter may perform filtering processing on input signals (for example, electrical signals detected by the electrode 104a and the electrode 104b) of the filter, to obtain electrical signals in a range of 0.5 Hz to 40 Hz, and an electrical signal at another frequency is filtered out. In some embodiments, the foregoing function of processing the electrical signals detected by the electrode 104a and the electrode 104b into the ECG waveform may be performed by another part, component, or circuit. The another part, component, or circuit may be a different part independent of a processor 103. The another part, component, or circuit may be built by using a separate device (for example, a semiconductor device). For example, the another part, component, or circuit may be an integrated circuit (integrated circuit, IC), a microcircuit (microcircuit), a chip (chip), a microchip (microchip), or the like that integrates an ECG detection function. This is not limited in this application.

The capacitance sensor 105 may be configured to detect a capacitance between a human body and the smart watch 100. The capacitance may reflect whether the human body is in good contact with the smart watch 100. When the capacitance sensor 105 is disposed on the electrode 104a and/or the electrode 104b, the capacitance sensor 105 may detect a capacitance between the human body and the electrode 104a and/or the electrode 104b. When the capacitance detected by the capacitance sensor 105 is excessively large or excessively small, it indicates that the human body is in poor contact with the electrode 104a and/or the electrode 104b. When the capacitance detected by the capacitance sensor 105 is moderate, it indicates that the human body is in good contact with the electrode 104$a$ and/or the electrode 104$b$. Whether the human body is in good contact with the electrode affects detection of an electrical signal by the electrode, and further affects generation of an ECG waveform. Therefore, when generating the ECG waveform, the smart watch 100 may determine, based on the capacitance detected by the capacitance sensor 106D, whether the user properly wears the smart watch 100.

The infrared spectroscopy 106 is configured to perform wearing status detection based on different reflection values of different substances.

The inertial measurement unit 107 is configured to measure a three-axis attitude angle (or an angular rate) and an acceleration that are of an object. In some embodiments, the inertial measurement unit 107 includes three uniaxial accelerometers and three uniaxial gyroscopes. The accelerometer detects an acceleration signal of an object on three independent axes of a coordinate system of a carrier. The gyroscope detects an angular velocity signal of the carrier relative to a navigation coordinate system, measures an angular velocity and an acceleration of the object in three-dimensional space, and calculates an attitude of the object based on the angular velocity and the acceleration. In some embodiments of this application, wearing part information of the smart watch 100 on a wrist of the user may be detected.

The memory 108 is configured to store a software program and data. The processor 103 runs the software program and the data that are stored in the memory 108, to perform various function applications and data processing of the smart watch 100. For example, in some embodiments of this application, the memory 108 may store a human body ECG waveform generated by the ECG detection module 103, a capacitance that is between the human body and the electrode 104$a$ and/or the electrode 104$b$ and that is collected by the capacitance sensor 105, and data such as an attitude angle and an acceleration that are measured by the inertial measurement unit 107.

The communication module 109 may be configured to enable the smart watch 100 to communicate with another electronic device, and is connected to a network by using the another electronic device. For example, in some embodiments of this application, the smart watch 100 may establish a connection to a server by using the communication module 109, and send ECG data generated by the smart watch 100 to the server. The server analyzes a heart function of the user based on the received ECG data, generates an electrocardiogram report, and sends the generated report to the smart watch 100 by using the communication module 109.

It may be understood that FIG. 2 shows merely an example structure for implementing a function of the smart watch 100 in the technical solutions of this application. A smart watch 100 that has another structure and can implement a similar function is also applicable to the technical solutions of this application. This is not limited herein.

Figure 3A:
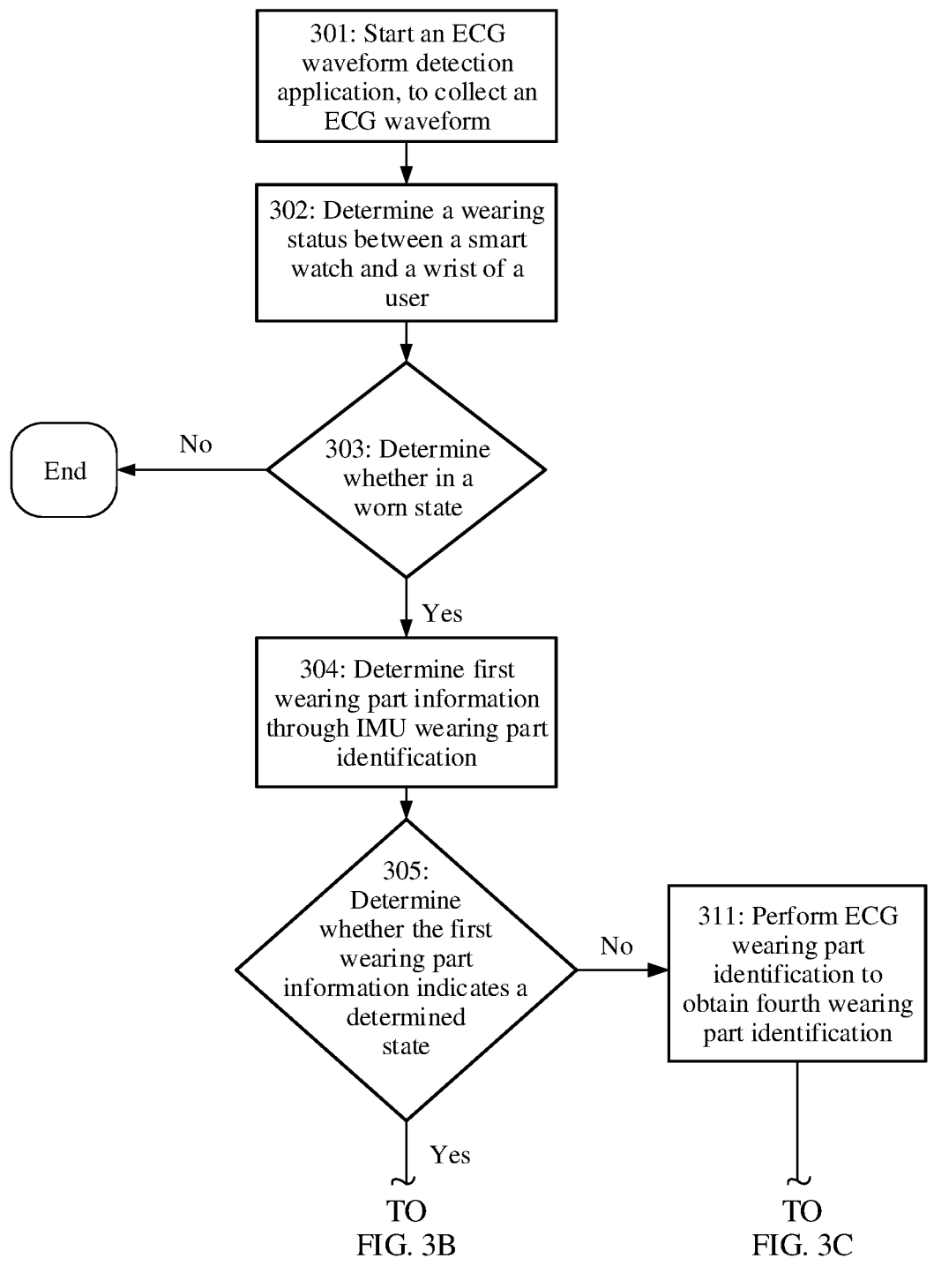
Figure 3C:
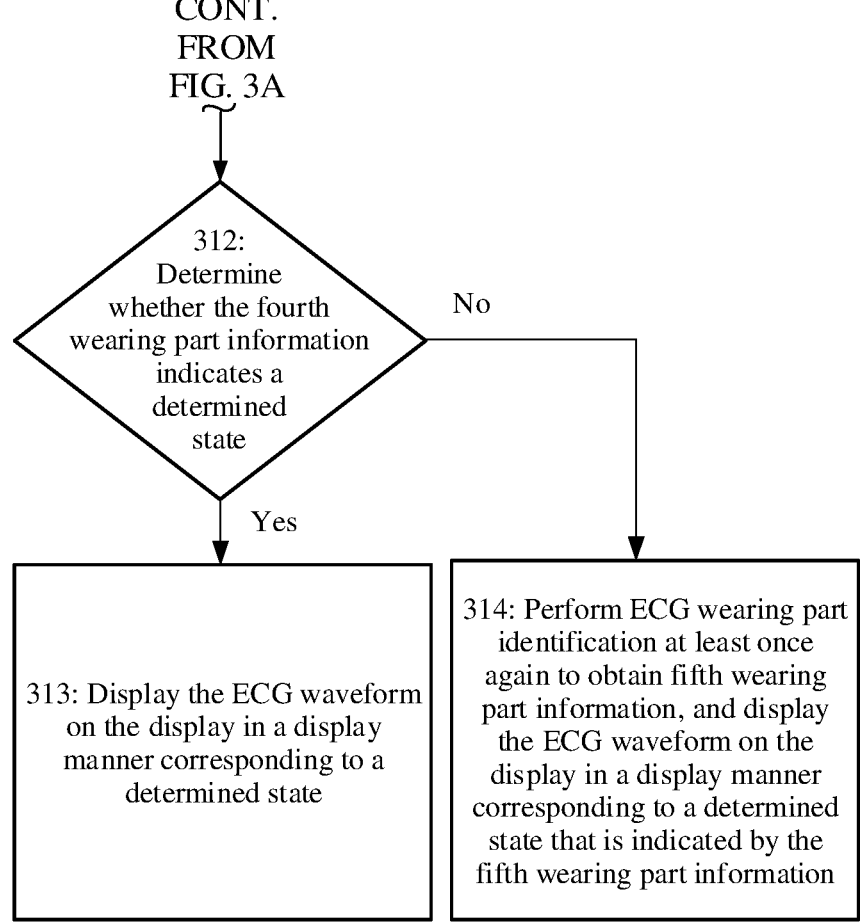

The following describes in detail the technical solutions of this application by using an example in which the user performs ECG detection by using the smart watch 100. FIG. 3A to FIG. 3C are a schematic flowchart of an ECG waveform display method according to some embodiments of this application. As shown in FIG. 3A to FIG. 3C, specifically, the method includes the following.

When a user wears the smart watch 100 on a left hand, and the left hand is used as a specified part, that is, the user wears the smart watch 100 on a left wrist, the smart watch 100 displays an ECG waveform on the display in a normal display manner. For example, a peak of the ECG waveform faces a left-hand side. However, when the user wears the smart watch 100 on a right wrist of the user, and does not perform the ECG waveform display method provided in this embodiment of this application, the smart watch 100 displays an ECG waveform on the display in an abnormal display manner. An example in which a direction of a waveform displayed on the display in a normal display manner is opposite to a direction of a waveform displayed on the display in an abnormal display manner, for example, a case in which a peak of an ECG waveform faces a right-hand side, is used for description.

Step 301: A smart watch 100 starts an ECG waveform detection application, to collect an ECG waveform.

In some embodiments, the smart watch 100 has an ECG waveform detection function. When an application that corresponds to the ECG waveform detection function and that is in the smart watch 100 is started, and the smart watch 100 enables the ECG waveform detection function. For example, when the user taps an ECG waveform detection APP by using a finger, as shown in FIG. 1A, or when the user sends, to the smart watch 100 in a voice manner, a command for starting an ECG waveform detection APP, the smart watch 100 detects a tap operation for starting the ECG waveform detection APP or receives a command for starting the ECG APP. When a hand of the user is in contact with an electrode on a side surface of the smart watch, that is, the ECG waveform detection application is enabled, the smart watch 100 starts ECG waveform detection, to collect an ECG waveform.

Step 302: The smart watch 100 determines a wearing status between the smart watch 100 and a wrist of the user.

After starting the ECG waveform detection application, the smart watch 100 collects an ECG waveform, and determines a wearing status and a wearing part, so that the ECG waveform of the smart watch 100 is displayed on the display in a normal display manner.

In some embodiments, a wearing status detection function of the smart watch 100 is implemented based on different impedance values of a capacitance in a worn state and a capacitance in a not-worn state. For example, when the user wears the smart watch 100, it is detected that an impedance value of a human body surface is in a range of 2 kΩ to 10 kΩ. In this case, the smart watch 100 learns that the smart watch 100 is in a worn state on the wrist of the user. When the user does not wear the smart watch 100, a detected impedance value of a human body surface is generally greater than 1 MΩ. In this case, the smart watch 100 learns that the smart watch 100 is in a not-worn state on the wrist of the user.

In addition, in some other embodiments, the smart watch 100 reads wearing status data between the smart watch 100 and the wrist of the user, and determines a wearing status between the smart watch 100 and the wrist of the user. Specifically, the method includes the following: The smart watch 100 reads a wearing status flag bit in a register of the smart watch 100, to obtain a wearing status between the smart watch 100 and the wrist of the user. For example, before the smart watch 100 starts the ECG waveform detection application, the smart watch 100 determines a value of the wearing status flag bit flag_wear in a flag register based on different impedance values of the capacitance in a worn state and the capacitance in a not-worn state. When the user wears the smart watch 100, it is detected that the impedance value of the human body surface is in the range of 2 kΩ to 10 kΩ, and the wearing status flag bit flag_wear in the flag register in the smart watch 100 is assigned a value of 1. When the smart watch 100 reads that the wearing status flag bit in the register of the smart watch 100 is 1, the smart watch 100 learns that the smart watch 100 is in a worn state on the wrist of the user. When the user does not wear the smart watch 100, the detected impedance value of the human body surface is generally greater than 1 MΩ, and the wearing status flag bit flag_wear in the flag register in the smart watch 100 is assigned a value of 0. When the smart watch 100 reads that the wearing status flag bit in the register of the smart watch 100 is 0, the smart watch 100 learns that the smart watch 100 is in a not-worn state on the wrist of the user.

In addition, different from the foregoing embodiment, in some other embodiments, according to a principle that reflection values of infrared rays on different substances are different, an infrared spectrum in a worn state and an infrared spectrum in a not-worn state that are detected by an infrared spectrum detection device are different. Therefore, the smart watch 100 may further implement the wearing status detection function of the smart watch 100 by using the infrared spectrum detection device.

Step 303: The smart watch 100 determines whether the smart watch 100 is in a worn state. If the smart watch 100 is in a worn state, step 304 is performed; otherwise, it indicates that the watch is not in a worn state, and in this case, IMU wearing part detection cannot be activated. Therefore, when a determining result in step 303 is no, a current process ends.

Step 304: The smart watch 100 determines first wearing part information through IMU wearing part identification.

In some embodiments, after the user wears the smart watch 100, the IMU obtains time-changing data of an attitude angle of a gyroscope, and time-changing data of an acceleration of an accelerometer. The smart watch 100 obtains an IMU wearing part detection confidence level (used as an example of a first wearing part confidence level) based on the time-changing data of the attitude angle and the time-changing data of the acceleration, and obtains IMU wearing part detection information (used as an example of the first wearing part information) based on the IMU wearing part detection confidence level. The following specifically describes the IMU wearing part detection confidence level. It may be understood that the IMU wearing part detection confidence level is used to determine authenticity probabilities of a left-hand wearing part, a right-hand wearing part, and an uncertain wearing part. The IMU wearing part detection confidence level may be a left-hand wearing confidence level, a right-hand wearing confidence level, or an uncertain wearing part detection confidence level. A sum of the left-hand wearing confidence level, the right-hand wearing confidence level, and the uncertain wearing part detection confidence level is 1. For example, the left-hand wearing confidence level is 0.8, the right-hand wearing confidence level is 0.1, and the uncertain wearing part confidence level is 0.1. The wearing information is determined, based on a highest confidence level, to indicate a left-hand wearing state. The wearing part information may indicate a left-hand wearing part, a right-hand wearing part, or an uncertain wearing part. In some embodiments, the IMU wearing part detection confidence level may be in a form of a percentage. This is not limited in this application. It may be understood that a sum of a left-hand wearing confidence level, a right-hand wearing confidence level, and an uncertain wearing part detection confidence level that are of a same detection may be 100%.

Specifically, that the IMU wearing part detection information (an example of the first wearing part information) is determined based on an acceleration value and the attitude angle that are detected by an IMU includes the following.

The smart watch 100 processes time-changing attitude angle data once every preset time interval, for example, 200 milliseconds, to obtain a standard deviation and an average value that are of an attitude angle within each preset time interval.

Figure 4:
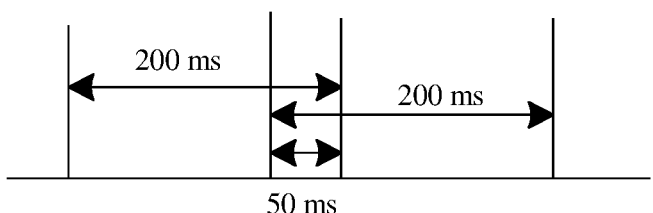
FIG. 4 is a schematic diagram of a time region of a collection periodicity whose preset interval is of 200 milliseconds and step is of 150 milliseconds according to some embodiments of this application.

The acceleration may be a change of the accelerometer on an X axis, a Y axis, and a Z axis, and the attitude angle may be a change of the gyroscope on Pitch (the Y axis), Roll (the X axis), or Yaw (the Z axis). For example, FIG. 4 is a schematic diagram of a time region of a collection periodicity whose preset interval is of 200 milliseconds and step is of 150 milliseconds according to some embodiments of this application. As shown in FIG. 4, after the user wears the watch, the smart watch 100 processes data of the gyroscope and the accelerometer once every preset time interval, for example, 200 milliseconds, where data of consecutive 200 ms has an overlapping area of 50 ms.

Figure 5:
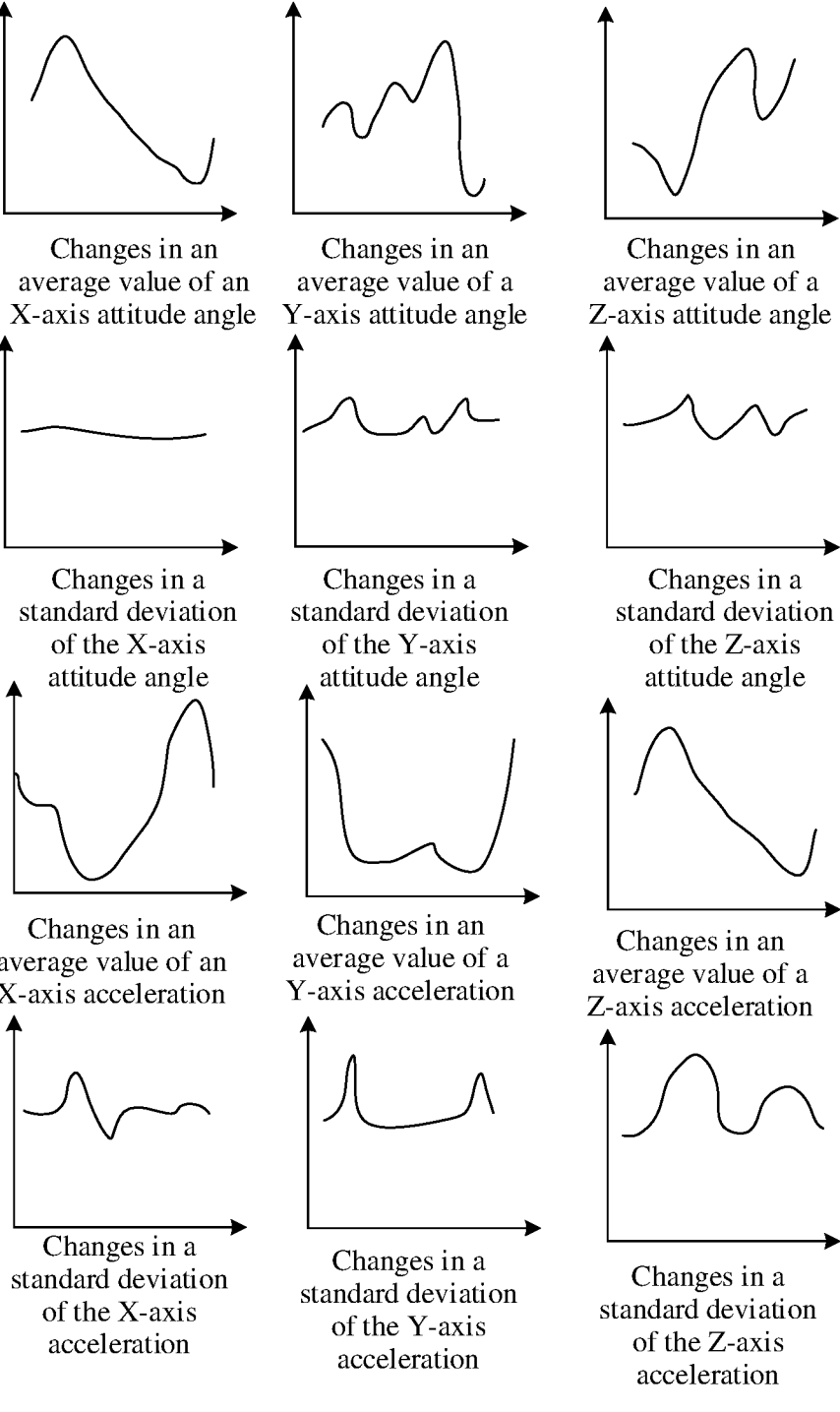
FIG. 5 is a schematic diagram of a waveform in which a difference and a standard value of an attitude angle and a difference and a standard value of an acceleration change with time according to some embodiments of this application.

In some embodiments, normalization processing is performed for changes of accelerations of the accelerometer on the X-axis, the Y-axis, and the Z-axis and changes of attitude angles such as Pitch (the Y-axis), Roll (the X-axis), and Yaw (the Z-axis) of the gyroscope in every 200 ms, and then parameters such as a standard deviation and an average value of corresponding accelerations and attitude angles are calculated. FIG. 5 shows a schematic diagram of a waveform in which a difference and a standard value of an attitude angle and a difference and a standard value of an acceleration change with time according to some embodiments of this application. As shown in FIG. 5, the following changes are included. A first column includes: changes in an average value of an X-axis attitude angle, changes in a standard deviation of the X-axis attitude angle, changes in an average value of an X-axis acceleration, and changes in a standard deviation of the X-axis acceleration. A second column includes: changes in an average value of a Y-axis attitude angle, changes in a standard deviation of the Y-axis attitude angle, changes in an average value of a Y-axis acceleration, and changes in a standard deviation of the Y-axis acceleration. A third column includes: changes in an average value of a Z-axis attitude angle, changes in a standard deviation of the Z-axis attitude angle, changes in an average value of a Z-axis acceleration, and changes in a standard deviation of the Z-axis acceleration. The gyroscope has attitude angles on three axes: X, Y, and Z, and is used to determine a direction of a moving object. Movement directions of the left hand and the right hand of the user are different. Accordingly, attitude angle data of the left hand and the right hand measured by the gyroscope is different. In a same time period, changes of attitude angle average values on three axes X, Y, and Z reflect an attitude angle average value in the time period. The standard deviation of the attitude angle reflects distribution and dispersion of attitude angle values in a time period. The average value and the standard deviation of the attitude angle can reflect a wearing part.

The acceleration is a vector, and a direction of the acceleration is a direction of a velocity change (quantity) of an object, and is the same as a direction of joint external forces. If a force is applied leftward or rightward, that is, different accelerations are provided, a speed of the force changes (including a rate and a direction). However, a leftward acceleration and a rightward acceleration clearly cause different effects. Force-applying directions of the left hand and the right hand in a movement process are usually different, and accelerations and acceleration directions are different. Therefore, a wearing part may be determined based on an average value and a standard deviation of the accelerations.

A distribution rule of the left and right hands and a standard for determining the left and right hands are obtained through algorithm model training. The following describes an example of an IMU wearing part identification model.

The standard deviation and average value of the accelerations of the accelerometer on the X-axis, the Y-axis, and the Z-axis, the standard deviation and average value of the attitude angles of the gyroscope on the Y-axis, the X-axis, and the Z-axis, and left-hand and right-hand state labels are input into the IMU wearing part identification model. A trained IMU wearing part identification model that meets a preset loss function is obtained by training the IMU wearing part identification model.

The currently obtained standard deviation and average value of accelerations of the accelerometer on the X-axis, the Y-axis, and the Z-axis, and the standard deviation and average value of the attitude angles of the gyroscope on the Pitch (Y-axis), the Roll (X-axis), and the Yaw (Z-axis) are input into the trained IMU wearing part identification model. An output result of the trained IMU wearing part identification model is the IMU wearing part detection confidence level and/or the IMU wearing part detection information. It may be understood that the IMU wearing part detection confidence level may be a left-hand wearing IMU wearing part detection confidence level, a right-hand wearing IMU wearing part detection confidence level, or an uncertain wearing part detection confidence level. The IMU wearing part detection information may indicate a left-hand wearing part, a right-hand wearing part, or an uncertain wearing part. For example, the IMU left-hand wearing detection confidence level is 0.8, the IMU right-hand wearing detection confidence level is 0.2, and the uncertain wearing part detection confidence level is 0.4. The IMU wearing part detection confidence level may be a decimal or a percentage. However, the IMU wearing part detection confidence level is not limited thereto.

Wearing part data may include a left/right-hand wearing flag hand_flag_imu. A value of the left/right-hand wearing flag hand_flag_imu is determined based on a left-hand wearing state, and the value of the left/right-hand wearing flag hand_flag_imu may be 0, 1, or 2. A value 0 indicates that it is uncertain whether the smart watch is worn on the left hand or the right hand, a value 1 indicates that the smart watch is worn on the left hand, and a value 2 indicates that the smart watch is worn on the right hand. The smart watch 100 reads the value of the left/right-hand wearing flag hand_flag_imu, to determine wearing part information.

In some embodiments, a plurality of IMU wearing part detection confidence levels are obtained based on the acceleration values and the attitude angles that are detected by the IMU. The plurality of IMU wearing part detection confidence levels are processed according to a first iteration formula, to obtain an average IMU wearing part confidence level (used as an example of the first average wearing part confidence level). The IMU wearing part detection information is determined based on the average IMU wearing part confidence level.

It may be understood that the first iteration formula may be as follows:

$$CI1\_average = a1*CI1\_average + b1*CI\_imui \qquad \text{(formula 1)}$$

In the formula, CI1_average represents the average IMU wearing part confidence level, and CI_imui represents the IMU wearing part detection confidence level, that is, a single confidence level CI_imui. a1 and b1 are natural numbers, a sum of a1 and b1 is 1, and a1 is greater than b1. The symbol "*" represents multiplication, and a value range of CI_average is [0,1]. For example, a1 is set to 0.6, and b2 is set to 0.4.

In some embodiments, that the IMU wearing part detection information is determined based on an IMU wearing part detection confidence level obtained in a single measurement specifically includes the following.

When the IMU wearing part detection confidence level is greater than a first threshold (for example, 0.7), it is determined that the smart watch is worn on the left hand. Alternatively, when the IMU wearing part detection confidence level is less than a second threshold (for example, 0.3), it is determined that the smart watch is worn on the right hand. Alternatively, when the IMU wearing part detection confidence level falls within an interval (for example, from 0.3 to 0.7) between a first threshold and a second threshold, it is determined that the wearing part is uncertain. The first threshold is greater than the second threshold.

For example, CI_imu represents the IMU wearing part detection confidence level, and hand_flag represents a wearing part flag bit. When a value of CI_imu is greater than 0.7, it is determined that the smart watch is worn on the left hand, and hand_flag is assigned a value 1. Alternatively, when a value of CI_imu is less than 0.3, it is determined that the smart watch is worn on the right hand, and hand_flag is equal to 2. Alternatively, when a value of CI_imu falls within an interval [0.3, 0.7], it is determined that the wearing part is uncertain, and hand_flag is equal to 0. The smart watch may determine the IMU wearing part detection information by reading the wearing part flag bit.

In addition, in some embodiments, when the average IMU wearing part confidence level is greater than a third threshold (for example, 0.7), it is determined that the smart watch is worn on the left hand. Alternatively, when the average IMU wearing part confidence level is less than a fourth threshold (for example, 0.3), it is determined that the smart watch is worn on the right hand. Alternatively, when the average IMU wearing part confidence level falls within an interval (for example, from 0.3 to 0.7) between a third threshold and a fourth threshold, it is determined that the wearing part is uncertain. The third threshold is greater than the fourth threshold.

For example, CI1_average represents the average IMU wearing part confidence level, and hand_flag represents a wearing part flag bit. When a value of CI1_average is greater than 0.7, it is determined that the smart watch is worn on the left hand, and hand_flag is assigned a value 1. Alternatively, when a value of CI1_average is less than 0.3, it is determined that the smart watch is worn on the right hand, and hand_flag is equal to 2. Alternatively, when a value of CI1_average falls within an interval [0.3, 0.7], it is determined that the wearing part is uncertain, and hand_flag is equal to 0. The smart watch may determine the IMU wearing part detection information by reading the wearing part flag bit.

Step 305: The smart watch 100 determines whether the first wearing part information indicates a determined state, and performs step 306 when the first wearing part information indicates a determined state, or performs step 311 when the first wearing part information does not indicate a determined state.

The IMU wearing part detection information is used as an example of the first wearing part information. When the smart watch 100 determines that the IMU wearing part detection information indicates a determined state, verification needs to be further performed by using an identification result obtained through ECG wearing part identification, to obtain an accurate wearing part detection result. In other words, step 306 is performed. When the smart watch 100 determines that the IMU wearing part detection information indicates an uncertain state, a wearing part identification result is directly obtained by using an identification result obtained through ECG wearing part identification. In other words, step 311 is performed.

Step 306: The smart watch 100 displays ECG wearing part identification prompt information on the display thereof to indicate the user to choose whether to perform ECG wearing part identification, so as to ensure that an ECG waveform is displayed in a normal state.

Figure 6:
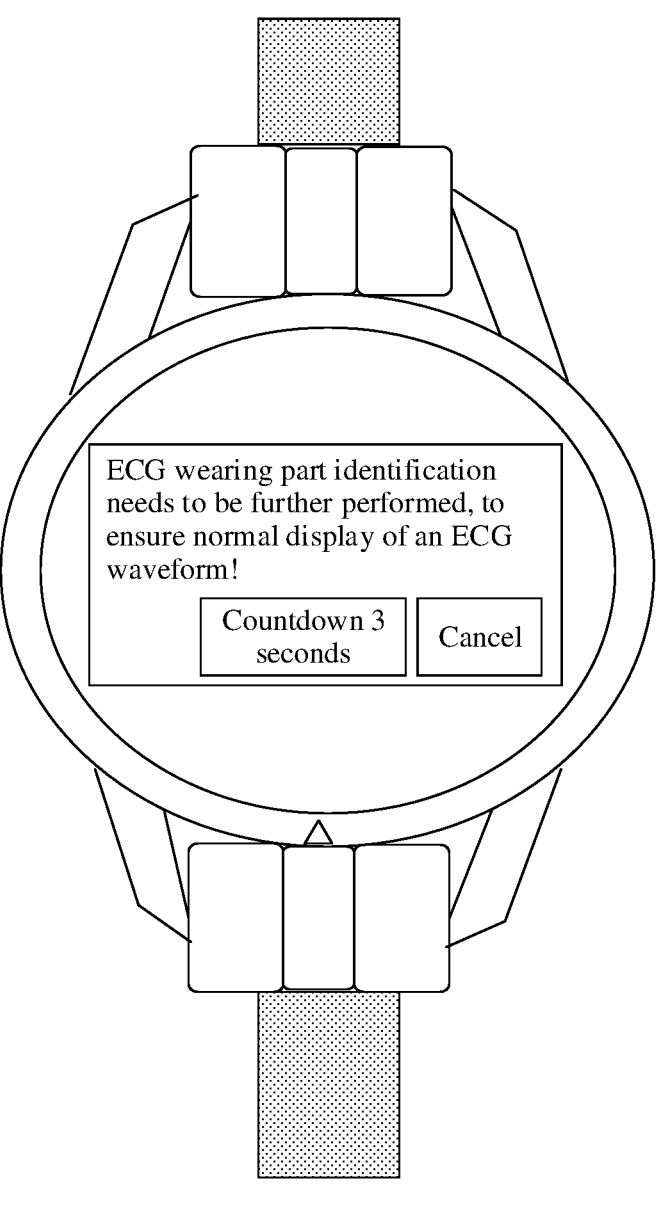
FIG. 6 is an example of a display interface diagram of ECG wearing part identification prompt information according to some embodiments of this application.

FIG. 6 is an example of a display interface diagram of ECG waveform detection prompt information according to some embodiments of this application. As shown in FIG. 6, a smart watch 100 displays, on a display thereof, prompt information that "ECG wearing part identification needs to be further performed, to ensure normal display of an ECG waveform!" and two options: "Countdown 3 seconds" and "Cancel". The option of "Countdown 3 seconds" indicates that ECG wearing part identification automatically starts when the time expires. According to an implementation of this application, ECG waveform detection is performed after IMU detection is performed, so that a wrist identification success rate is improved, and an electrocardiogram waveform displayed in a normal manner is provided for a user. Therefore, a manner of "Countdown to 3 seconds" is adopted to automatically perform ECG waveform detection, unless the user forcibly stops the operation. When the user taps a "Cancel" icon, the smart watch 100 does not obtain an ECG wearing part identification request, and cancels displaying of the prompt information that "ECG wearing part identification needs to be further performed, to ensure normal display of an ECG waveform!" and the two options: "Countdown 3 seconds" and "Cancel".

In addition, different from the case in the foregoing embodiments, in some other embodiments, the user may alternatively tap, based on a requirement of the user, an "ECG wearing part identification" icon after tapping the "Cancel" icon for a period of time, to enable ECG wearing part identification.

In addition, in some other embodiments, the smart watch 100 does not display the ECG wearing part identification prompt information on the display thereof to indicate the user to choose whether to perform ECG wearing part identification. Instead, the smart watch 100 directly and automatically performs ECG wearing part identification after performing IMU wearing part identification.

In this way, in some embodiments, a left/right-hand determining result is obtained based on wearing part information and an ECG wearing part detection confidence level that are obtained through ECG wearing part identification. Alternatively, a left/right-hand determining result is obtained by comprehensively considering wearing part information and an IMU wearing part detection confidence level that are obtained through IMU wearing part identification and wearing part information and an ECG wearing part detection confidence level that are obtained through ECG wearing part identification.

Step 307: When obtaining the ECG wearing part identification request, the smart watch 100 determines second wearing part information through ECG wearing part identification.

In some embodiments, an "ECG wearing part identification" icon is tapped, to enable ECG wearing part identification.

In addition, in some other embodiments, as shown in FIG. 6, the option of "Countdown 3 seconds" indicates that ECG wearing part identification automatically starts when the time expires.

In some embodiments, that the smart watch 100 obtains the ECG wearing part detection confidence level based on waveform feature information of the ECG waveform after obtaining an ECG waveform detection request includes:

obtaining an average ECG wearing part confidence level (used as an example of a second average wearing part confidence level) based on the IMU wearing part detection confidence level and the ECG wearing part detection confidence level; and determining the ECG wearing part information (an example of second wearing part information) based on the average ECG wearing part confidence level.

Specifically, in some embodiments, the method includes:

obtaining a plurality of ECG wearing part detection confidence level based on the waveform feature information of the ECG waveform;

obtaining the average ECG wearing part detection confidence level (as an example of the second average wearing part confidence level) based on an average IMU wearing part confidence level (used as an example of a first average wearing part confidence level), the plurality of ECG wearing part detection confidence levels (used as an example of the second wearing part confidence level), and a second iteration formula; and obtaining ECG wearing part detection information based on the average ECG wearing part detection confidence level.

The second iteration formula is as follows:

$$CI2\_average=a2*CI1\_average+b2*CI\_ecgi \qquad \text{(formula 2)}$$

In the formula, CI2_average represents the average ECG wearing part confidence level, CI1_average represents the average IMU wearing part confidence level, CI_ecgi represents the ECG wearing part detection confidence level, a2 and b2 are natural numbers, a sum of a2 and b2 is 1, and a2 is less than b2. It is considered that there may be a time interval between ECG wearing part identification and IMU wearing part identification. Therefore, a weight coefficient before the confidence level is determined based on a length of the time interval. For example, longer time away from IMU wearing part identification and detection indicates a larger value of b2. For example, a2 is set to 0.4, and b2 is set to 0.6. A value range of CI_ecgi is [0, 1]. It may be understood that, in some other embodiments, when a user is a patient with arrhythmia and an ECG waveform is deformed, an IMU pre-determining proportion is increased, to improve accuracy and reduce time used for ECG collection. Specifically, the method includes the following.

The smart watch 100 displays, on a display interface of the display, prompt information that the user inputs a physical condition; and when arrhythmia information input by the user on the display interface of the smart watch 100 is obtained, the IMU pre-determining proportion b2 is increased.

In some embodiments, when the average ECG wearing part detection confidence level is greater than a fifth threshold, it is determined that the smart watch is worn on the left hand. Alternatively, when the average ECG wearing part detection confidence level is less than a sixth threshold, it is determined that the smart watch is worn on the right hand.

Alternatively, when the average ECG wearing part detection confidence level falls within an interval between a fifth threshold and a sixth threshold, it is determined that the wearing part is uncertain. The fifth threshold is greater than the sixth threshold.

For example, left and right demarcation thresholds are set to T1_ECG and T1_exg, where T1_ECG is greater than or equal to T1_exg. When values of CI_ecgi are within [T1_ECG,1] and [0,T1_exg), the values of CI_ecgi respectively correspond to the left hand and the right hand, and values of hand_flag_ecg respectively correspond to assigned values 1 and 2. When a value of CI_ecgi is within an interval [T1_exg, T1_ECG], a left/right-hand state is uncertain. It is assumed that a value of T1_ECG is 0.5, and a value of T1_exg is 0.3. When the value of CI_ecgi is within an interval [0.5,1], the value of CI_ecgi corresponds to the left hand, and the value of hand_flag_ecg corresponds to the value 1. Alternatively, when the value of CI_ecgi is within [0, 0.3), the value of CI_ecgi corresponds to the right hand, and the value of hand_flag_ecg corresponds to the value 2. Alternatively, when the value of CI_ecgi is within an interval [0.3, 0.5], a left/right-hand state is uncertain. In some embodiments, the smart watch 100 may obtain the ECG wearing part detection information by reading hand_flag_ecg.

In addition, in some other embodiments, different from the case in the foregoing implementations, the ECG wearing part detection confidence level is only processed by using a third iteration formula, to obtain the average ECG wearing part confidence level (used as an example of the second average wearing part confidence level), and the ECG wearing part detection information is obtained based on the average ECG wearing part confidence level.

The third iteration formula is as follows:

$$CI2\_average = a2*CI2\_average + b2*CI\_ecgi \quad \text{(formula 3)}$$

In the formula, CI2_average represents the average ECG wearing part confidence level, CI_ecgi represents the ECG wearing part detection confidence level, a2 and b2 are natural numbers, a sum of a2 and b2 is 1, and a2 is less than b2. It is considered that there may be a time interval between ECG wearing part identification and IMU wearing part identification. Therefore, a weight coefficient before the confidence level is determined based on a length of the time interval. For example, longer time away from IMU wearing part identification and detection indicates a larger value of b2. For example, a2 is set to 0.4, and b2 is set to 0.6. A value range of CI_ecgi is [0, 1].

In addition, in some other embodiments, the ECG wearing part detection information is obtained based on the ECG wearing part confidence level once.

The following describes how to obtain the ECG wearing part detection confidence level by using an example. In some embodiments, after the user wears the smart watch 100, left/right-hand identification is performed based on an EGG waveform. According to a function of an ECG wearing part identification algorithm, an ECG waveform form at an initial detection stage of the user is analyzed, to determine a part at which the user wears an intelligent wearable device. An ECG waveform (such as an R wave and a QRS complex width) within a time period of t (for example, 1s to 2s) is extracted, to implement left/right-hand determining. Specifically, the method includes:

obtaining a segment (for example, duration of 1s) of ECG waveform after the user wears the smart watch 100;
    determining waveform feature information of the obtained segment of ECG waveform;

Inputting the waveform feature information of the ECG waveform into a trained ECG wearing part identification model, to obtain an output result of the trained ECG wearing part identification model that is the ECG wearing part detection confidence level; and determining the ECG wearing part detection information based on the ECG wearing part detection confidence level. The ECG wearing part detection information may be about whether the smart watch is worn on the left hand or the right hand. The ECG wearing part detection confidence level may be a left-hand wearing ECG confidence level or a right-hand wearing ECG confidence level.

Figure 7:
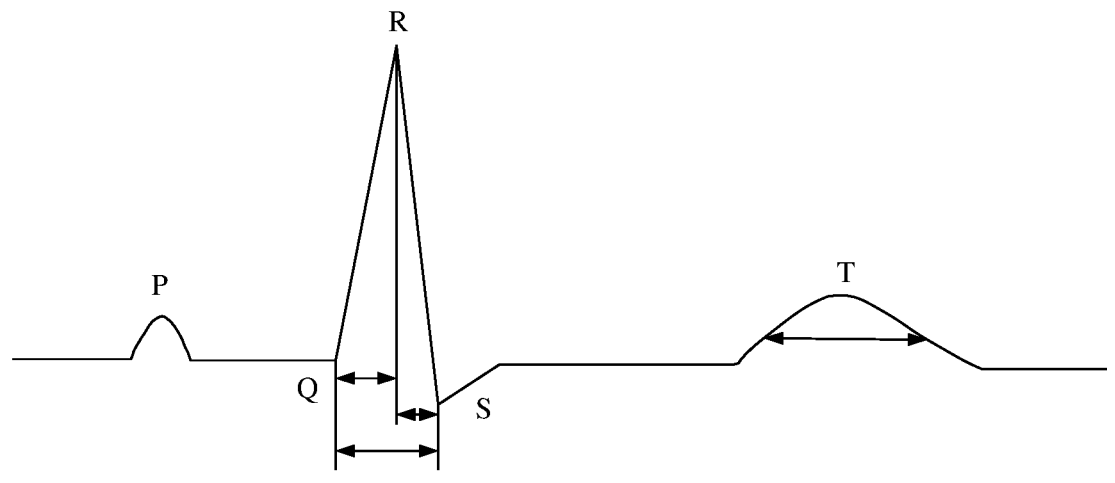
FIG. 7 is a schematic diagram of a segment of ECG waveform according to some embodiments of this application.

It may be understood that, in ECG detection, the extracted waveform feature information of the ECG waveform may include: QRS wave area, a ratio of a QR width to an RS width, a QR height, an RS height, a P wave amplitude, P wave area (including positive and negative values), a T wave width, and T wave area. FIG. 7 is a schematic diagram of a segment of ECG waveform according to some embodiments of this application. As shown in FIG. 7, the ECG waveform includes QRS wave area, a ratio of a QR width to an RS width, a QR height, an RS height, a P wave amplitude, P wave area (including positive and negative values), a T wave width, and T wave area. Principal element reconstruction is performed on a signal based on principal element analysis, and first three principal element features that have largest changes and that are in waveform feature information are selected. The selected principal element features are input into the trained ECG wearing part identification model, to implement left/right-hand determining based on the ECG waveform, and obtain the confidence level CI_ecgi.

Step 308: The smart watch 100 determines whether the first wearing part information is the same as the second wearing part information, and performs step 309 when the first wearing part information is the same as the second wearing part information, or performs step 310 when the first wearing part information is different from the second wearing part information.

The IMU wearing part detection information is used as an example of the first wearing part information, and the ECG wearing part detection information is used as an example of the second wearing part information. That the IMU wearing part detection information is the same as the ECG wearing part detection information means that results of IMU wearing part identification and ECG wearing part identification are consistent. Accordingly, it may be determined that the IMU wearing part detection information and the ECG wearing part detection information indicate a left-hand wearing state or a right-hand wearing state in a determined state. Therefore, the smart watch 100 may continue to perform step 309. That the IMU wearing part detection information is different from the ECG wearing part detection information means that results of IMU wearing part identification and ECG wearing part identification are inconsistent. Accordingly, it cannot be determined whether the IMU wearing part detection information and the ECG wearing part detection information indicate a left-hand wearing state or a right-hand wearing state in a determined state. ECG wearing part identification is relatively accurate. Therefore, ECG wearing part identification needs to be further performed, to obtain a wearing part identification result. The smart watch 100 may continue to perform step 310.

Step 309: The smart watch 100 displays the ECG waveform on the display in a display manner corresponding to a determined state.

In this embodiment of this application, according to preset wearing part information that is determined based on a hardware structure such as an electrode A and an electrode B, the smartphone 100 is set to be worn on the left hand. It may be understood that in another embodiment, the preset wearing part information may alternatively indicate a right-hand wearing state. When the wearing part information is the preset wearing part information, the ECG waveform is displayed on the display in a normal display manner. It may be understood that, in another embodiment, the preset wearing part information may alternatively indicate a left-hand wearing state. When the IMU wearing part detection information and the ECG wearing part detection information are left-hand wearing information or right-hand wearing information, the IMU wearing part detection information and the ECG wearing part detection information indicate a determined state.

In some embodiments, when the IMU wearing part detection information (used as an example of the first wearing part information) and the ECG wearing part detection information (used as an example of the second wearing part information) are the same as the preset wearing part information, the smart watch 100 displays the ECG waveform on the display in a normal display manner.

For example, the preset wearing part information indicates a left-hand wearing state. When the IMU wearing part detection information and the ECG wearing part detection information are the same as the left-hand wearing information, the smart watch 100 displays the ECG waveform on the display in a normal display manner corresponding to the left-hand wearing state.

It may be understood that, in some other embodiments, when the IMU wearing part detection information and the ECG wearing part detection information are different from the preset wearing part information, the smart watch 100 adjusts an abnormal display manner to a normal display manner, to display the ECG waveform on the display.

For example, the preset wearing part information indicates a left-hand wearing state. When the IMU wearing part detection information and the ECG wearing part detection information are different from the left-hand wearing information, the smart watch 100 adjusts an abnormal display manner to a normal display manner, to display the ECG waveform on the display.

Figure 8:
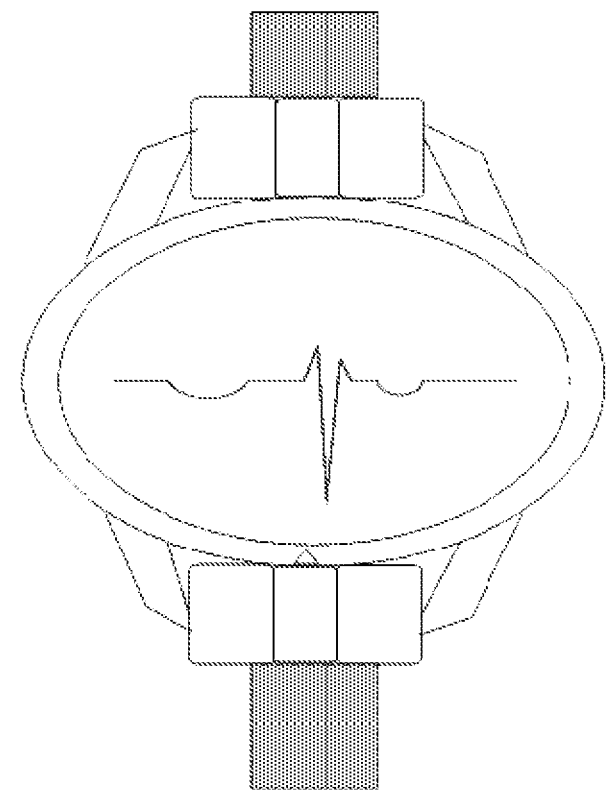
FIG. 8 is an example of a display interface diagram of an ECG waveform displayed in an abnormal display manner according to some embodiments of this application.

FIG. 8 is an example of a display interface diagram of an ECG waveform displayed in an abnormal display manner according to some embodiments of this application. When the user wears the smart watch 100 on a left wrist of the user, the smart watch 100 displays the ECG waveform on the display in a normal display manner. However, when the user wears the smart watch 100 on a right wrist of the user, the smart watch 100 displays the ECG waveform in a negative direction of a coordinate axis, that is, in a direction towards a right-hand side. As shown in FIG. 8, a display status of the ECG waveform on the display of the smart watch 100 is that the ECG waveform is displayed in an abnormal display manner.

Figure 9:
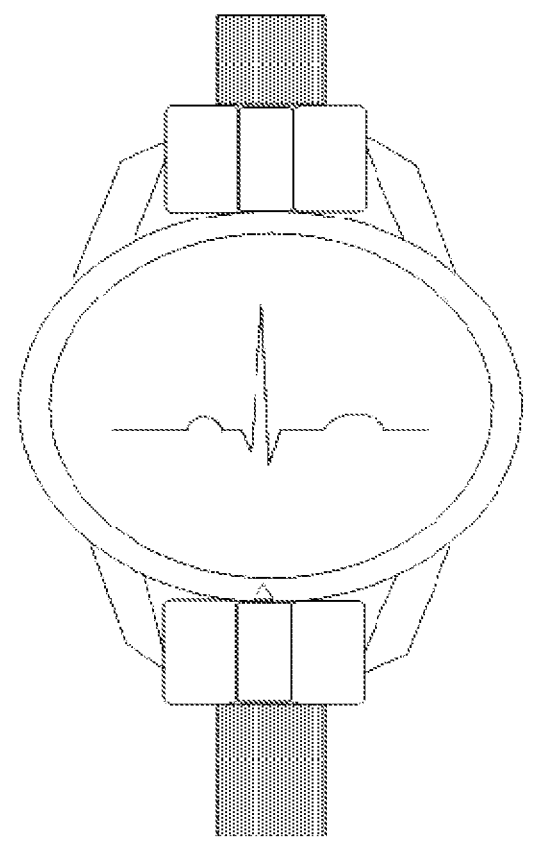
FIG. 9 is an example of a display interface diagram of an ECG waveform displayed in a normal display manner according to some embodiments of this application.

FIG. 9 is an example of a display interface diagram of an ECG waveform displayed in a normal display manner according to some embodiments of this application. As shown in FIG. 9, a display status of the ECG waveform on the display of the smart watch 100 is that the ECG waveform is displayed in a normal display manner. To be specific, waveform data in FIG. 9 is multiplied by a negative 1, so that the waveform is reversed, and the ECG waveform is displayed in a positive direction of a coordinate axis, that is, in a direction towards a left-hand side.

In this application, wearing part information is determined through IMU wearing part identification and ECG wearing part identification, to determine whether the ECG waveform is displayed in a normal display manner. If the ECG waveform is not displayed in a normal display manner, the ECG waveform is adjusted to an ECG waveform displayed in a normal display manner. In this way, a false positive rate caused by only performing IMU wearing part identification can be reduced, and a problem of excessively long time consumption caused by only performing ECG wearing part identification can be reduced. An identification time period is shortened, and at the same time, accuracy of wearing part identification and accuracy of displaying an ECG waveform in a normal state are improved.

Step 310: The smart watch 100 performs ECG wearing part identification at least once again to obtain third wearing part information, and the smart watch 100 displays the ECG waveform on the display in a display manner corresponding to a determined state that is indicated by the third wearing part information.

In some embodiments, when wearing part information obtained through IMU wearing part identification is different from wearing part information obtained through ECG wearing part identification, the smart watch 100 continues to perform ECG wearing part identification for at least once, to obtain the ECG wearing part detection information (used as an example of the third wearing part information) and the ECG wearing part detection confidence level. In a manner of determining a wearing status based on a result of further performing EGC wearing part identification, the following example implementations may be included.

In an implementation, ECG wearing part identification is performed at least once again to obtain the third wearing part information, that is, a quantity of times of ECG wearing part identification is increased. An average ECG wearing part detection confidence level (used as a third average wearing part confidence level) is re-obtained based on a plurality of ECG wearing part detection confidence levels (used as an example of a second wearing part confidence level) obtained based on the increased quantity of times of ECG wearing part identification and the average ECG wearing part detection confidence level (used as an example of a second average wearing part confidence level). ECG wearing part detection information (used as an example of the third wearing part information) is determined based on the re-obtained average ECG wearing part detection confidence level.

A calculation formula for re-obtaining the average ECG wearing part detection confidence level is as follows:

$$CI3average = a3*CI2\_average + b3*CIN\_CI\_ecgi \qquad \text{(formula 4)}$$

In the formula, CI3_average represents the re-obtained average ECG wearing part detection confidence level, CI2_average represents the average ECG wearing part detection confidence level, CIN_CI_ecgi represents the ECG wearing part detection confidence level corresponding to the increased quantity of times of ECG waveform detection, a3 and b3 are natural numbers, a sum of a3 and b3 is 1, and a3 is less than b3.

Left and right demarcation thresholds are set to T1_CI3 and T1_ci3, where T1_ECG is greater than or equal to T1_CI3. When values of CI3_average are within [T1_CI3,1] and [0,T1_ci3), the values of Ci3_average respectively correspond to the left hand (a value of hand_flag_ecg is equal to 1) and right hand (a value of hand_flag_ecg is equal to 2). When a value of CI3_average is within an interval [T1_ci3, T1_CI3], a left/right-hand state is uncertain.

For example, when the value of hand_flag_ecg and a value of hand_flag are both 1 or 2, a corresponding ECG waveform is displayed. For example, when the value of hand_flag is equal to 1 (the value of hand_flag_ecg is equal to the value of hand_flag and is equal to 1), the ECG waveform is displayed in a forward direction. Alternatively, when the value of hand_flag is equal to 2 (the value of hand_flag_ecg is equal to the value of hand_flag and is equal to 2), the ECG waveform is displayed in a reverse direction, that is, ECG waveform data is multiplied by −1.

It may be understood that, in some embodiments, when the user performs measurement immediately after wearing the watch, a quantity of times of IMU-based determining is small, and prediction cannot be performed correctly. In this case, a waveform feature pre-determining proportion is increased. Accuracy of waveform-based determining is higher than accuracy of IMU wearing part identification, so that accuracy of determining a left/right-hand wearing position and accuracy of displaying an ECG waveform in a normal display manner are improved.

In this way, both IMU wearing part identification and ECG wearing part identification are used, and when pieces of wearing information determined by the IMU wearing part identification and the ECG wearing part identification are different, a quantity of ECG wearing part identification times and an ECG detection confidence level proportion are increased. Therefore, to some extent, accuracy of displaying a wearing part and the ECG waveform in a normal state is improved.

In addition, in some other embodiments, ECG wearing part identification may be performed at least once again to directly obtain at least one third wearing part confidence level, and the third wearing part information is determined based on the at least one third wearing part confidence level.

For example, ECG wearing part identification is performed once again to obtain one ECG wearing part detection confidence level (used as an example of the third wearing part confidence level), and the third wearing part information is determined based on the ECG wearing part detection confidence level.

For example, the ECG wearing part detection confidence level is processed by using a fifth iteration formula, to obtain the average ECG wearing part confidence level (used as an example of the third average wearing part confidence level), and the ECG wearing part detection information is obtained based on the average ECG wearing part confidence level.

A calculation formula (as an example of the fifth iteration formula) for re-obtaining the average ECG wearing part detection confidence level is as follows:

$$CI3\_average=a3*CI3\_average+b3*CIN\_CI\_ecgi \qquad \text{(formula 5)}$$

In the formula, CI3_average represents the re-obtained average ECG wearing part detection confidence level, CIN_CI_ecgi represents the ECG wearing part detection confidence level corresponding to the increased quantity of times of ECG waveform detection, a3 and b3 are natural numbers, a sum of a3 and b3 is 1, and a3 is less than b3.

Next, as shown in FIG. 3A, the process returns to the determining in step S05. When a determining result in this step is no, processing in step S311 is performed.

Step 311: The smart watch 100 performs ECG wearing part identification to obtain fourth wearing part identification.

In some embodiments, ECG wearing part identification may be performed at least once again to directly obtain at least one ECG wearing part detection confidence level (used as an example of the fourth wearing part confidence level), and the ECG wearing part detection information (used as an example of the fourth wearing part position information) is determined based on the at least one ECG wearing part detection confidence level.

For example, ECG wearing part identification is performed once again to obtain one ECG wearing part detection confidence level (used as an example of the fourth wearing part confidence level), and the ECG wearing part detection information is determined based on the ECG wearing part detection confidence level.

In addition, in some other embodiments, the ECG wearing part detection confidence level is processed by using a sixth iteration formula, to obtain the average ECG wearing part confidence level (used as an example of the fourth average wearing part confidence level), and the ECG wearing part detection information (the fourth wearing part information) is obtained based on the average ECG wearing part confidence level.

For example, a calculation formula (as an example of the sixth iteration formula) for re-obtaining the average ECG wearing part detection confidence level is as follows:

$$CI6\_average=a6*CI6\_average+b6*CIN\_CI\_ecgi \qquad \text{(formula 6)}$$

In the formula, CI6_average represents the re-obtained average ECG wearing part detection confidence level, CIN_CI_ecgi represents the ECG wearing part detection confidence level corresponding to the increased quantity of times of ECG waveform detection, a6 and b6 are natural numbers, a sum of a6 and b6 is 1, and a6 is less than b6.

Step 312: The smart watch 100 determines whether the fourth wearing part information indicates a determined state, and performs step 313 when the fourth wearing part information indicates a determined state, or performs step 314 when the fourth wearing part information does not indicate a determined state.

Step 313: The smart watch 100 displays the ECG waveform on the display in a display manner corresponding to a determined state.

The embodiment of step 313 and the embodiment of step 309 are based on a same concept. Details are not described herein again.

Step 314: The smart watch 100 performs ECG wearing part identification at least once again to obtain fifth wearing part information; and the smart watch 100 displays the ECG waveform on the display in a display manner corresponding to a determined state that is indicated by the fifth wearing part information.

In some embodiments, ECG wearing part identification may be performed the at least once again to directly obtain at least one ECG wearing part detection confidence level (used as an example of the fifth wearing part confidence level), and the fifth wearing part information is determined based on the at least one ECG wearing part detection confidence level.

For example, ECG wearing part identification is performed once again to obtain one ECG wearing part detection confidence level (used as an example of the fifth wearing part confidence level), and the fifth wearing part information is determined based on the ECG wearing part detection confidence level.

In addition, in some other embodiments, the ECG wearing part detection confidence level is processed by using a seventh iteration formula, to obtain the average ECG wearing part confidence level (used as an example of the fifth average wearing part confidence level), and the ECG wearing part detection information (the fifth wearing part information) is obtained based on the average ECG wearing part confidence level.

For example, a calculation formula for re-obtaining the average ECG wearing part detection confidence level is as follows:

$$CI7\_average = a7*CI7\_average + b7*CIN\_CI\_ecgi \quad \text{(formula 7)}$$

In the formula, CI7_average represents the re-obtained average ECG wearing part detection confidence level, CIN_CI_ecgi represents the ECG wearing part detection confidence level corresponding to the increased quantity of times of ECG waveform detection, a7 and b7 are natural numbers, a sum of a7 and b7 is 1, and a7 is less than b7.

A conception of a process of determining the fifth wearing part information based on the ECG wearing part detection confidence level is similar to that of a process of obtaining the wearing part information according to the formula 1, the formula 2, or the formula 3. Details are not described herein again.

An embodiment of this application further provides a readable medium. The readable medium stores instructions. When the instructions are executed on a machine, the machine is enabled to perform the foregoing ECG waveform display method.

Optionally, in this embodiment, the foregoing storage medium may be located in at least one of a plurality of network servers in a computer network. Optionally, in this embodiment, the foregoing storage medium includes but is not limited to any medium that can store program code, such as a USB flash drive, a read-only memory (ROM, Read-Only Memory), a random access memory (RAM, Random Access Memory), a removable hard disk, a magnetic disk, or an optical disc.

An embodiment of this application further provides an electronic device. The electronic device includes:

a memory, configured to store instructions executed by one or more processors of the electronic device; and a processor that is one of the processors of the electronic device, is configured to perform the foregoing firewall rule configuration method. The electronic device has a function of implementing the foregoing ECG waveform display method. The functions may be implemented by hardware, or may be implemented by hardware executing corresponding software. The hardware or software includes one or more modules corresponding to the foregoing functions.

Figure 10:
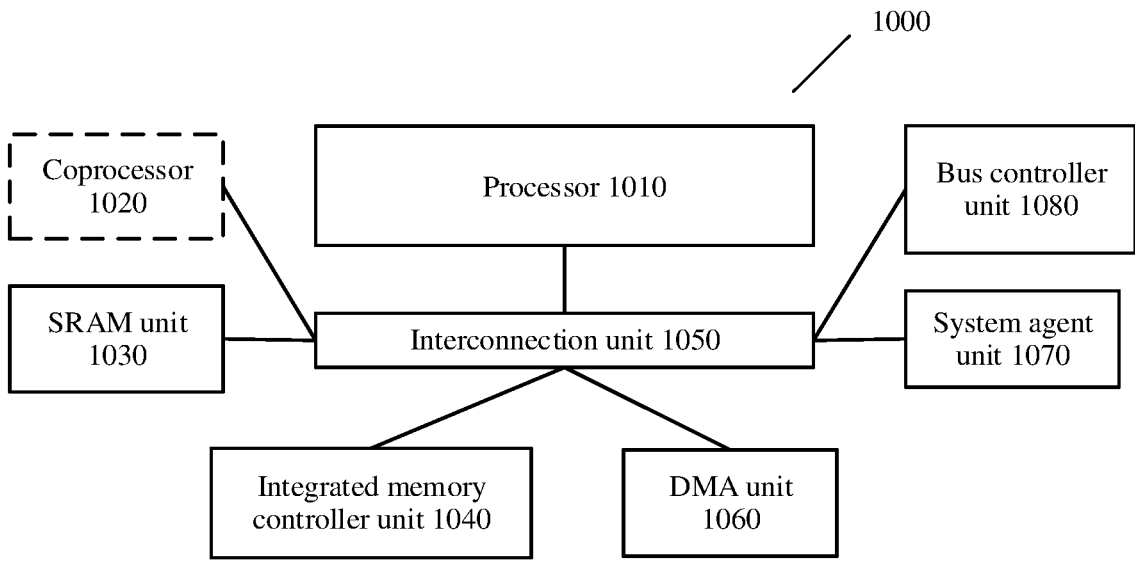
FIG. 10 is a block diagram of an electronic device on chip (SoC) according to some embodiments of this application.

According to an embodiment of this application, FIG. 10 is a block diagram of a SoC (System on Chip, system on chip) 1000. In FIG. 10, similar components have a same reference numeral. In addition, a dashed box is an optional feature of a more advanced SoC. In FIG. 10, the SoC 1000 includes: an interconnection unit 1050 coupled to an application processor 1010; a system agent unit 1070; a bus controller unit 1080; an integrated memory controller unit 1040; one group of coprocessors 1020 or one or more coprocessors 1020 that may include integrated graphics logic, an image processor, an audio processor, and a video processor; a static random access memory (SRAM) unit 1030; and a direct memory access (DMA) unit 1060.

In an embodiment, the coprocessor 1020 includes a dedicated processor, for example, a network or communication processor, a compression engine, a GPGPU, a high-throughput MIC processor, or an embedded processor.

Embodiments disclosed in this application may be implemented in hardware, software, firmware, or a combination of these implementation methods. Embodiments of this application may be implemented as a computer program or program code executed in a programmable system. The programmable system includes at least one processor, a storage system (including volatile and non-volatile memories and/or storage elements), at least one input device, and at least one output device.

The program code may be applied to input instructions, to perform functions of the ECG waveform display method described in this application and generate output information. The output information may be applied to one or more output devices in a known manner.

For a purpose of this application, a processing system includes any system having a processor such as a digital signal processor (DSP), a microcontroller, an application-specific integrated circuit (ASIC), or a microprocessor.

The program code may be implemented in a high-level procedural language or an object-oriented programming language, to communicate with the processing system. The program code may alternatively be implemented by using an assembly language or a machine language when needed. Actually, the mechanism described in this application is not limited to a scope of any particular programming language. In any case, the language may be a compiled language or an interpretive language.

Although this application has been illustrated and described with reference to some preferred embodiments of this application, a person of ordinary skill in the art should understand that various changes may be made to this application in form and details without departing from the spirit and scope of this application.

What is claimed is:

1. A method, comprising:

starting, by an electronic device, an electrocardiogram (ECG) waveform detection application, to collect an ECG waveform;

reading, by the electronic device, wearing part data between the electronic device and a wrist of a user, wherein the wearing part data is obtained through an inertial measurement unit (IMU) wearing part identification process;

determining, by the electronic device, first wearing part information based on the wearing part data, wherein the first wearing part information comprises a determined state or an uncertain state, and the determined state is a first determined state or a second determined state, wherein the first determined state is that a wearing state between the electronic device and the wrist of the user is a right-hand wearing state, and the second determined state is that a wearing state between the electronic device and the wrist of the user is a left-hand wearing state;

obtaining, by the electronic device, second wearing part information between the electronic device and the wrist of the user through an ECG wearing part identification process; and displaying, by the electronic device when the first wearing part information and the second wearing part information are the same and the first wearing part information comprises the first determined state or the second determined state, the ECG waveform on a display in a display manner corresponding to the first determined state or the second determined state.

2. The method according to claim 1, wherein displaying, when the first wearing part information and the second wearing part information are the same and the first wearing part information comprises the first determined state or the second determined state, the ECG waveform on the display in the display manner corresponding to the first determined state or the second determined state comprises:

displaying, by the electronic device, the ECG waveform on the display in a normal display manner when the first wearing part information and the second wearing part information are the same as preset wearing part information.

3. The method according to claim 1, wherein displaying, when the first wearing part information and the second wearing part information are the same and the first wearing part information comprises the first determined state or the second determined state, the ECG waveform on the display in the display manner corresponding to the first determined state or the second determined state comprises:

when the first wearing part information and the second wearing part information are different from preset wearing part information, adjusting, by the electronic device, the ECG waveform, to obtain an adjusted ECG waveform, and displaying the adjusted ECG waveform on the display in a normal display manner.

4. The method according to claim 1, further comprising:

when the first wearing part information and the second wearing part information respectively indicate the first determined state or the second determined state but are different from each other, performing the ECG wearing part identification process at least one more time to obtain third wearing part information; and displaying, by the electronic device, the ECG waveform on the display in a display manner corresponding to a determined state that is indicated by the third wearing part information.

5. The method according to claim 1, further comprising:

when the first wearing part information indicates the uncertain state, performing the ECG wearing part identification process again to obtain fourth wearing part information; and displaying, by the electronic device, the ECG waveform on the display in a display manner corresponding to a determined state that is indicated by the fourth wearing part information.

6. The method according to claim 5, further comprising:

when the first wearing part information and the fourth wearing part information are the same and indicate the uncertain state, performing the ECG wearing part identification process at least one more time to obtain fifth wearing part information; and displaying, by the electronic device, the ECG waveform on the display in a display manner corresponding to a determined state that is indicated by the fifth wearing part information.

7. The method according to claim 1, wherein determining, by the electronic device, the first wearing part information based on the wearing part data comprises:

obtaining a first wearing part confidence level based on the wearing part data, and determining the first wearing part information based on at least the first wearing part confidence level.

8. The method according to claim 7, wherein obtaining the first wearing part confidence level based on the wearing part data, and determining the first wearing part information based on at least the first wearing part confidence level comprises:

obtaining a plurality of first wearing part confidence levels based on the wearing part data;

processing the plurality of first wearing part confidence levels according to a first iteration formula, to obtain a first average wearing part confidence level; and determining the first wearing part information based on the first average wearing part confidence level.

9. The method according to claim 7, wherein the wearing part data comprises an acceleration value and an attitude angle that are detected by an IMU, and obtaining the first wearing part confidence level based on the wearing part data comprises:

obtaining the first wearing part confidence level based on the acceleration value and the attitude angle that are detected by the IMU.

10. The method according to claim 9, wherein obtaining the first wearing part confidence level based on the acceleration value and the attitude angle that are detected by the IMU comprises:

inputting a currently obtained standard deviation and average value of accelerations of an accelerometer on an X-axis, a Y-axis, and a Z-axis, and a standard deviation and average value of attitude angles of a gyroscope on the X-axis, the Y-axis, and the Z-axis into a trained IMU wearing part identification model, wherein an output result of the trained IMU wearing part identification model is the first wearing part confidence level.

11. The method according to claim 1, wherein obtaining the second wearing part information through the ECG wearing part identification process comprises:

obtaining a second wearing part confidence level through the ECG wearing part identification process, and determining the second wearing part information based on at least the second wearing part confidence level.

12. The method according to claim 11, wherein obtaining the second wearing part confidence level through the ECG wearing part identification process, and determining the second wearing part information based on at least the second wearing part confidence level comprises:

obtaining a plurality of first wearing part confidence levels based on the wearing part data;

processing the plurality of first wearing part confidence levels according to a first iteration formula, to obtain a first average wearing part confidence level;

determining the first wearing part information based on the first average wearing part confidence level;

obtaining a plurality of second wearing part confidence levels through the ECG wearing part identification process;

obtaining a second average wearing part confidence level based on the first average wearing part confidence level, the plurality of second wearing part confidence levels, and a second iteration formula; and obtaining the second wearing part information based on the second average wearing part confidence level.

13. The method according to claim 11, wherein obtaining the second wearing part confidence level through the ECG wearing part identification process comprises:

determining the second wearing part confidence level based on waveform feature information of the ECG waveform.

14. The method according to claim 13, wherein determining the second wearing part confidence level based on the waveform feature information of the ECG waveform comprises:

inputting the waveform feature information of the ECG waveform into a trained ECG wearing part identification model, to obtain an output result of the trained ECG wearing part identification model that is the second wearing part confidence level.

15. The method according to claim 14, wherein the waveform feature information of the ECG waveform comprises:

a QRS wave area, a ratio of a QR width to an RS width, a QR height, an RS height, a P wave amplitude, a P wave area (comprising positive and negative values), a T wave width, and a T wave area.

16. The method according to claim 4, wherein performing the ECG wearing part identification process at least one more time to obtain the third wearing part information comprises:

performing iteration processing on the second wearing part confidence level and a third wearing part confidence level, to obtain a third average wearing part confidence level, wherein the second wearing part confidence level is obtained through a previous ECG wearing part identification process, and the second wearing part confidence level corresponds to the second wearing part information; and determining the third wearing part information based on the third average wearing part confidence level.

17. An electronic device, comprising:

a memory, configured to store instructions executed by one or more processors of the electronic device; and the one or more processors, configured to execute the instructions, wherein executing the instructions enables the electronic device to perform:

starting an electrocardiogram (ECG) waveform detection application, to collect an ECG waveform;

reading wearing part data between the electronic device and a wrist of a user, wherein the wearing part data is obtained through an inertial measurement unit (IMU) wearing part identification process;

determining first wearing part information based on the wearing part data, wherein the first wearing part information comprises a determined state or an uncertain state, and the determined state is a first determined state or a second determined state, wherein the first determined state is that a wearing state between the electronic device and the wrist of the user is a right-hand wearing state, and the second determined state is that a wearing state between the electronic device and the wrist of the user is a left-hand wearing state;

obtaining second wearing part information between the electronic device and the wrist of the user through an ECG wearing part identification process; and displaying, when the first wearing part information and the second wearing part information are the same and the first wearing part information comprises the first determined state or the second determined state, the ECG waveform on a display in a display manner corresponding to the first determined state or the second determined state.

18. The electronic device according to claim 17, wherein executing the instructions further enables the electronic device to perform:

displaying the ECG waveform on the display in a normal display manner when the first wearing part information and the second wearing part information are the same as preset wearing part information.

19. A non-transitory computer-readable medium, wherein the computer-readable medium stores instructions, and when the instructions are executed, the instructions enable an electronic device to perform:

starting an electrocardiogram (ECG) waveform detection application, to collect an ECG waveform;

reading wearing part data between the electronic device and a wrist of a user, wherein the wearing part data is obtained through an inertial measurement unit (IMU) wearing part identification process;

determining first wearing part information based on the wearing part data, wherein the first wearing part information comprises a determined state or an uncertain state, and the determined state is a first determined state or a second determined state, wherein the first determined state is that a wearing state between the electronic device and the wrist of the user is a right-hand wearing state, and the second determined state is that a wearing state between the electronic device and the wrist of the user is a left-hand wearing state;

obtaining second wearing part information between the electronic device and the wrist of the user through an ECG wearing part identification process; and displaying, when the first wearing part information and the second wearing part information are the same and the first wearing part information comprises the first determined state or the second determined state, the ECG waveform on a display in a display manner corresponding to the first determined state or the second determined state.

20. The non-transitory computer-readable medium according to claim 19, wherein displaying, when the first wearing part information and the second wearing part information are the same and the first wearing part information comprises the first determined state or the second determined state, the ECG waveform on the display in the display manner corresponding to the first determined state or the second determined state comprises:

displaying the ECG waveform on the display in a normal display manner when the first wearing part information and the second wearing part information are the same as preset wearing part information.

* * * * *